US009701944B2

(12) United States Patent
Tangy et al.

(10) Patent No.: US 9,701,944 B2
(45) Date of Patent: *Jul. 11, 2017

(54) INFECTIOUS CDNA OF AN APPROVED VACCINE STRAIN OF MEASLES VIRUS, USE FOR IMMUNOGENIC COMPOSITIONS

(71) Applicants: Frederic Tangy, Les Lilas (FR); Chantal Combredet, Levallois (FR); Valerie Labrousse-Najburg, Crespieres (FR); Michel Brahic, Saint Germain en Laye (FR)

(72) Inventors: Frederic Tangy, Les Lilas (FR); Chantal Combredet, Levallois (FR); Valerie Labrousse-Najburg, Crespieres (FR); Michel Brahic, Saint Germain en Laye (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/667,088

(22) Filed: Mar. 24, 2015

(65) Prior Publication Data

US 2015/0275184 A1  Oct. 1, 2015

Related U.S. Application Data

(63) Continuation of application No. 11/013,786, filed on Dec. 17, 2004, now Pat. No. 9,005,961, which is a continuation of application No. PCT/EP03/07145, filed on Jun. 20, 2003.

(30) Foreign Application Priority Data

Jun. 20, 2002  (FR) .................................. 02 291551

(51) Int. Cl.
*C07K 14/005* (2006.01)
*C12N 15/86* (2006.01)
*C12N 7/00* (2006.01)
*A61K 39/00* (2006.01)

(52) U.S. Cl.
CPC .............. *C12N 7/00* (2013.01); *C07K 14/005* (2013.01); *C12N 15/86* (2013.01); *A61K 39/00* (2013.01); *A61K 2039/525* (2013.01); *A61K 2039/5254* (2013.01); *A61K 2039/5256* (2013.01); *C12N 2760/18421* (2013.01); *C12N 2760/18422* (2013.01); *C12N 2760/18434* (2013.01); *C12N 2760/18443* (2013.01); *C12N 2795/10243* (2013.01)

(58) Field of Classification Search
CPC ........... C12N 2795/10243; C12N 2740/16043; A61K 2039/5256; A61K 39/00; A61K 39/165
See application file for complete search history.

(56) References Cited

U.S. PATENT DOCUMENTS

| 5,654,136 | A | 8/1997 | Sasaki et al. |
|---|---|---|---|
| 6,146,642 | A | 11/2000 | Garcia-Sastre et al. |
| 7,402,429 | B1 | 7/2008 | Billeter et al. |
| 7,556,812 | B2 | 7/2009 | Tangy et al. |
| 7,851,214 | B2 | 12/2010 | Billeter et al. |
| 7,993,924 | B2 | 8/2011 | Billeter et al. |
| 8,158,416 | B2 | 4/2012 | Billeter et al. |
| 8,337,857 | B2 | 12/2012 | Tangy et al. |
| 8,586,364 | B2 | 11/2013 | Tangy et al. |
| 8,853,379 | B2 | 10/2014 | Tangy et al. |
| 8,859,240 | B2 | 10/2014 | Tangy et al. |
| 9,005,925 | B2 * | 4/2015 | Tangy .................. C07K 14/005 435/70.3 |
| 9,005,961 | B2 * | 4/2015 | Tangy .................. C07K 14/005 435/320.1 |
| 9,012,214 | B2 * | 4/2015 | Tangy ............... A61K 47/48776 435/320.1 |
| 2005/0186563 | A1 | 8/2005 | Hoffmann |
| 2005/0227224 | A1 | 10/2005 | Tangy et al. |
| 2006/0013826 | A1 | 1/2006 | Tangy et al. |
| 2007/0280961 | A1 | 12/2007 | Billeter et al. |
| 2008/0124803 | A1 | 5/2008 | Billeter et al. |
| 2011/0129493 | A1 | 6/2011 | Mendiretta et al. |
| 2012/0003264 | A1 | 1/2012 | Billeter et al. |
| 2012/0121538 | A1 | 5/2012 | Glueck et al. |
| 2013/0052218 | A1 | 2/2013 | Tangy et al. |

FOREIGN PATENT DOCUMENTS

| EP | 0440219 | 8/1991 |
|---|---|---|
| WO | 97/06270 | 2/1997 |
| WO | 98/37911 | 9/1998 |

(Continued)

OTHER PUBLICATIONS

Advisory Action dated Mar. 19, 2009, in U.S. Appl. No. 11/014,842.
Office Action dated Sep. 16, 2008, in U.S. Appl. No. 11/014,842.
Office Action dated Nov. 5, 2007, in U.S. Appl. No. 11/014,842.
Christopher L. Parks, et al.; "Comparison of Predicted Amino Acid Sequences of Measles Virus Strains in the Edmonston Vaccine Lineage"; Journal of Virology; pp. 910-920; vol. 75, No. 2; (Jan. 2001).
Frank Radecke, et al.; "Rescue of Measles Viruses from Cloned DNA"; The EMBO Journal, Oxford University Press; pp. 5773-5784; vol. 14, No. 23; (Dec. 1, 1995).

(Continued)

*Primary Examiner* — Bao Li
(74) *Attorney, Agent, or Firm* — Arrigo, Lee & Guttman LLP

(57) ABSTRACT

The invention relates to a cDNA molecule which encodes the nucleotide sequence of the full length antigenomic (+)RNA strand of a measles virus (MV) originating from an approved vaccine strain. It also concerns the preparation of immunogenic compositions using said cDNA.

14 Claims, 17 Drawing Sheets

(56) References Cited

FOREIGN PATENT DOCUMENTS

| WO | 01/03744 | 1/2001 |
|---|---|---|
| WO | 01/09309 | 2/2001 |

OTHER PUBLICATIONS

Office Action mailed Sep. 25, 2013, in U.S. Appl. No. 12/476,304.
Office Action mailed Feb. 24, 2014, in U.S. Appl. No. 12/476,304.
Ballad, Isidro, et al., "Infectious measles virus from cloned DNA," The EMBO Journal, vol. 9, No. 2, pp. 379-384 (1990).
Ballad, Isidro, et al., "Infectious measles virus from cloned cDNA," The EMBO Journal, vol. 10, No. 11, p. 3558 (1991).
Schmid, Anita, et al., "A procedure for selective full length cDNA cloning of specific RNA species," Nucleic Acid Research, vol. 15, No. 10, pp. 3987-3996 (1987).
Genbank locus AF266286.1, Measles virus strain Edmonston (AIK-C vaccine), complete genome. Jan. 25, 2001.
Genbank locus AF266287.1, Measles virus strain Edmonston (Moraten vaccine), complete genome. Jan. 25, 2001.
Genbank locus AF266289.1, Measles virus strain Edmonston (Rubeovax vaccine), complete genome. Jan. 25, 2001.
Genbank locus AF266290.1, Measles virus strain Edmonston (Zagreb vaccine), complete genome. Jan. 25, 2001.
Genbank locus AF266291.1, Measles virus strain Edmonston (Schwarz vaccine), complete genome. Jan. 25, 2001.
Parks et al (Journal of Virology 73:3560-3566, 1999).
Escoffier et al (Journal of Virology 73:5220-5224, 1999).
Borges et al (Mem. Inst. Oswaldo Cruz 91:507-514, 1996).
Duprex et al (Journal of Virology 73:9568-9575, 1999).
Singh et al (Journal of General Virology 80:101-106, 1999).
Ndumbe et al (Vaccine 13:276-280, 1995).
Pugachev et al (Journal of Virology 71:562-568, 1997).
van Binnendijk RS, van der Heijden RW, Osterhaus AD. Monkeys in measles research. Curr Top Microbiol Immunol. 1995; 191:135-48.
Libman MD, Ibrahim SA, Omer MI, Adlan IA, Bellavance F, Hoskins E, Berney F, Ward B. No evidence for short or long term morbidity after increased titer measles vaccination in Sudan. Pediatr Infect Dis J. Feb. 2002;21(2):112-9.
Walsh EP, Baron MD, Anderson J, Barrett T. Development of a genetically marked recombinant rinderpest vaccine expressing green fluorescent protein. J Gen Virol. Mar. 2000;81(Pt 3):709-18.
Mortimer EA, Jr. "Communicable Diseases". p. 245. Pless IB. Ed. The Epidemiology of childhood disorders. Oxford University Press, 1994.
Stokes J Jr., Hilleman MR, Weibel RE, et al. Efficacy of live, attenuated measles-virus vaccine given with human immune globulin: a preliminary report. N Engl J Med 1961;265:507-13.
Yamanouchi K, Egashira Y, Uchida N, Kodama H, Kobune F. Giant cell formation in lymphoid tissues of monkeys inoculated with various strains of measles virus. Jpn J Med Sci Biol. Jun. 1970;23(3):131-45.
Mrkic B, Pavlovic J, Rulicke T, Volpe P, Buchholz CJ, Hourcade D, Atkinson JP, Aguzzi A, Cattaneo R. Measles virus spread and pathogenesis in genetically modified mice. J Virol. Sep. 1998;72(9):7420-7.
Tangy, F., et al. J. Virol. 63:1101-1106 (1989).
Burnstein T, et. al. Infect Immun. Dec. 1974;10(6)1 378-82.
Schneider H, et. al. J Virol Methods. Feb. 1997;64(1):57-64.
Takata CS, Kubrusly FS, Miyaki C, Mendes IF, de Rizzo E. [Susceptibility of Vero cell line to vaccine strains of the measles virus]. Rev Saude Publica. Jun. 1994;28(3):209-12.
Vesikari T, Ala-Laurila EL, Heikkinen A, Terho A, D'Hondt E, Andre FE. Clinical trial of a new trivalent measles-mumps-rubella vaccine in young children. Am J Dis Child. Sep. 1984;138(9).843-7.
Johnson JA, Heneine W. Characterization of endogenous avian leukosis viruses in chicken embryonic fibroblast substrates used in production of measles and mumps vaccines. J Virol. Apr. 2001;75(8).3605-12.

Buchanan R, Bonthius DJ. Measles virus and associated central nervous system sequelae. Semin Pediatr Neurol. Sep. 2012;19(3):107-14.
Bitnun A, Shannon P, Durward A, Rota PA, Bellini WJ, Graham C, Wang E, Ford-Jones EL, Cox P, Becker L, Fearon M, Petric M, Tellier R. Measles inclusion-body encephalitis caused by the vaccine strain of measles virus. Clin Infect Dis. Oct. 1999;29(4):855-61.
Zhang X, Rennick LJ, Duprex WP, Rima BK. Determination of spontaneous mutation frequencies in measles virus under nonselective conditions. J Virol. Mar. 2013;87(5).2686-92. Epub Dec. 19, 2012.
Plumet S, Duprex WP, Gerlier D. Dynamics of viral RNA synthesis during measles virus infection. J Virol. Jun. 2005;79 (11).6900-8.
Collins PL, Bukreyev A, Murphy BR. What are the risks—hypothetical and observed—of recombination involving live vaccines and vaccine vectors based on nonsegmented negative-strain RNA viruses? J Virol. Oct. 2008;82(19):9805-6.
Betakova T, Svetlikova D, Gocnik M. Overview of measles and mumps vaccine: origin, present, and future of vaccine production. Acta Virol. 2013;57(2).91-6.
NCBI GenBank Sequence Acc. No. AF266291. Direct Submission. Jan. 25, 2001.
Centers for Disease Prevention and Control (CDC). Measles: Pink Sheet; May 2012.
Office Action May 21, 2013 in parent U.S. Appl. No. 11/013,786.
Fukuda A, et. al. Jpn J Med Sci Biol. Dec. 1983;36(6):331-5.
Herold et al. Poliovirus requires a precise 5' end for efficient positive-strand RNA synthesis. Journal of Virology 2000, vol. 74, No. 14, pp. 6394-6400.
Tangy et al. Molecular cloning of the complete genome of strain GDVII of Theiler's virus and production of infectious transcripts. Journal of Virology 1989, vol. 63, No. 3, pp. 1101-1106.
Wang et al.; "Recombinant Measles Viruses Expressing Heterologous Antigens of Mumps and Simian Immunodeficiency Viruses"; Vaccine, vol. 19, pp. 2329-2336, (2001).
Takeda et al., Recovery of Pathogenic Measles Virus From Cloned cDNA; Journal of Virology, vol. 74, No. 14, pp. 6643-6647, (2000).
Tangy et al.; "Measles Vaccine as a Potential Vector for AIDS Vaccination"; AIDS Vaccine Conference, Sep. 5-8, 2001, Abstract No. 225.
Singh et al.:, "A Recombinant Measles Virus Expressing Hepatitis B Virus Surface Antigen Induces Humoral Immune Responses in Genetically Modified Mice"; Journal of Virology, vol. 73, No. 6, pp. 4823-4828, (1999).
Spielhofer et al.; "Chimeric Measles Virus With a Foreign Envelope"; Journal of Virology, vol. 72, No. 3, pp. 2150-2159, (1998).
Schlereth et al.; "Successful Vaccine-Induced Seroconversion by Single-Dose Immunization in the Presence of Measles Virus-Specific Maternal Antibodies"; Journal of Virology, vol. 74, No. 10, pp. 4652-4657, (2000).
Ruggli et al., "Nucleotide Sequence of Classical Swine Fever Virus Strain Alfort/187 and Transcription of Infectious RNA From Stably Cloned Full-Length cDNA"; Journal of Virology, vol. 70, No. 6, pp. 3478-3487, (1996).
Rice et al., "Production of Infectious RNA Transcripts From Sindbis Virus cDNA Clones: Mapping of Lethal Mutations, Rescue of a Temperature-Sensitive Marker, and in Vitro Mutagenesis to Generate Defined Mutants"; vol. 61, No. 12, pp. 3809-3819, (1987).
Konstantin et al., "Improvement of the Specific Infectivity of the Rubella Virus (RUB) Infectious Clone: Determinants of Cytopathogenicity Induced by RUB Map to the Nonstructural Proteins"; Journal of Virology, vol. 71, No. 1, pp. 562-568, (1997).
Despres et al., "Live Measles Vaccine Expressing the Secreted Form of the West Nile Virus Envelope Glycoprotein Protects Against West Nile Virus Encephalitis"; J. Infect. Dis. vol. 191, pp. 207-214 (2005).
Partial European Search Report for EP 02 29 1550 (foreign counterpart of U.S. Appl. No. 11/014,842), Feb. 7, 2003.
International Search Report for PCT/EP 03/07146 (foreign counterpart of U.S. Appl. No. 11/014,842), Apr. 16, 2004.
Office Action dated Aug. 6, 2009, in co-pending U.S. Appl. No. 11/014,842.

* cited by examiner

Sequence of ATU:

actagcctacctccatcattgttataaaaacttaggaaccagtccacacagccgccagtccatcaacgtacgtagcgcgcATGGTGAGCAAGGGCGAGGAGCTGTT
CACCGGGGTGGTGCCCATCCTGGTCGAGCTGGACGGCGACGTAAACGGCCACAAGTTCAGCGTGTCCGGCGAGGGCGAG
GGCGATGCCACCTACGGCAAGCTGACCCTGAAGTTCATCTGCACCACCGGCAAGCTGCCCGTGCCCTGGCCCACCCTCGT
GACCACCCTGACCTACGGCGTGCAGTGCTTCAGCCGCTACCCCGACCACATGAAGCAGCACGACTTCTTCAAGTCCGCCA
TGCCCGAAGGCTACGTCCAGGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACGGCAACATCCTGGGGCACAA
GCTGGAGTACAACTACAACAGCCACAACGTCTATATCATGGCCGACAAGCAGAAGAACGGCATCAAGGTGAACTTCAAG
ATCCGCCACAACATCGAGGACGGCAGCGTGCAGCTCGCCGACCACTACCAGCAAAACACCCCCATCGGCGACGGCCCCG
TGCTGCTGCCCGACAACCACTACCTGAGCACCCAGTCCGCCCTGAGCAAAGACCCCAACGAGAAGCGCGATCACATGGT
CCTGCTGGAGTTCGTGACCGCCGCCGGGATCACTCTCGGCATGGACGAGCTGTACAAGTAGtgagcgcgcagcgctgacgtctcgcgatC
gatgctagc

FIG 4B

```
GCGGCCGCTA ATACGACTCA CTATAGGGcc aactttgttt ggtctgatga gtccgtgagg   60
acgaaaccog gagtcccggg tcACCAAACA AAGTTGGGTA AGGATAGTTC AATCAATGAT  120
CATCTTCTAG TGCACTTAGG ATTCAAGATC CTATTATCAG GGACAAGAGC AGGATTAGGG  180
ATATCCGAGA TGGCCACACT TTTAAGGAGC TTAGCATTGT TCAAAAGAAA CAAGGACAAA  240
CCACCCATTA CATCAGGATC CGGTGGAGCC ATCAGAGGAA TCAAACACAT TATTATAGTA  300
CCAATCCCTG GAGATTCCTC AATTACCACT CGATCCAGAC TTCTGGACCG GTTGGTGAGG  360
TTAATTGGAA ACCCGGATGT GAGCGGGCCC AAACTAACAG GGGCACTAAT AGGTATATTA  420
TCCTTATTTG TGGAGTCTCC AGGTCAATTG ATTCAGAGGA TCACCGATGA CCCTGACGTT  480
AGCATAAGGC TGTTAGAGGT TGTCCAGAGT GACCAGTCAC AATCTGGCCT TACCTTCGCA  540
TCAAGAGGTA CCAACATGGA GGATGAGGCG GACCAATACT TTTCACATGA TGATCCAATT  600
AGTAGTGATC AATCCAGGTT CGGATGGTTC GGGAACAAGG AAATCTCAGA TATTGAAGTG  660
CAAGACCCTG AGGGATTCAA CATGATTCTG GGTACCATCC TAGCCCAAAT TTGGGTCTTC  720
CTCGCAAAGG CGGTTACGGG CCCAGACACG GCAGCTGATT CGGAGCTAAG AAGGTGGATA  780
AAGTACACCC AACAAAGAAG GGTAGTTGGT GAATTTAGAT TGGAGAGAAA ATGGTTGGAT  840
GTGGTGAGGA ACAGGATTGC CGAGGACCTC TCCTTACGCC GATTCATGGT CGCTCTAATC  900
CTGGATATCA AGAGAACACC CGGAAACAAA CCAGGATTG CTGAAATGAT ATGTGACATT  960
GATACATATA TCGTAGAGGC AGGATTAGCC AGTTTTATCC TGACTATTAA GTTTCGGATA 1020
GAAACTATGT ATCCTGCTCT TGGACTGCAT GAATTTGCTG GTGAGTTATC CACACTTGAG 1080
TCCTTGATGA ACCTTTACCA GCAAATGGGG GAAACTGCAC CCTACATGGT AATCCTGGAG 1140
AACTCAATTC AGAACAAGTT CAGTGCAGGA TCATACCCTC TGCTCTGGAG CTATGCCATG 1200
GGAGTAGGAG TGGAACTTGA AAACTCCATG GGAGGTTTGA ACTTTGGCCG ATCTTACTTT 1260
GATCCAGCAT ATTTTAGATT AGGGCAAGAG ATGGTAAGGA GGTCAGCTGG AAAGGTCAGT 1320
TCCACATTGG CATCTGAACT CGGTATCACT GCCGAGGATG CAAGGCTTGT TTCAGAGATT 1380
GCAATGCATA CTACTGAGGA CAAGATCAGT AGAGCGGTTG GACCCAGACA AGCCCAAGTA 1440
TCATTTCTAC ACGGTGATCA AAGTGAGAAT GAGCTACCGA GATTGGGGGG CAAGGAAGAT 1500
AGGAGGGTCA AACAGAGTCG AGGAGAAGCC AGGGAGAGCT ACAGAGAAAC GGGGCCCAGC 1560
AGAGCAAGTG ATGCGAGAGC TGCCCATCTT CCAACCGGCA CACCCCTAGA CATTGACACT 1620
GCAACGGAGT CCAGCCAAGA TCCGCAGGAC AGTCGAAGGT CAGCTGACGC CCTGCTTAGG 1680
CTGCAAGCCA TGGCAGGAAT CTCGGAAGAA CAAGGCTCAG ACACGGACAC CCCTATAGTG 1740
TACAATGACA GAAATCTTCT AGACTAGGTG CGAGAGGCCG AGGGCCAGAA CAACATCCGC 1800
CTACCATCCA TCATTGTTAT AAAAAACTTA GGAACCAGGT CCACACAGCC GCCAGCCCAT 1860
CAACCATCCA CTCCCACGAT TGGAGCCAAT GGCAGAAGAG CAGGCACGCC ATGTCAAAAA 1920
CGGACTGGAA TGCATCCGGG CTCTCAAGCC CGAGCCCATC GGCTCACTGG CCATCGAGGA 1980
AGCTATGGCA GCATGGTCAG AAATATCAGA CAACCACGGA CAGGAGCGAG CCACCTGCAG 2040
GGAAGAGAAG GCAGGCAGTT CGGGTCTCAG CAAACCATGC CTCTCAGCAA TTGGATCAAC 2100
TGAAGGCGGT GCACCTCGCA TCCGCGGTCA GGGACCTGGA GAGAGCGATG AGGACGCTCA 2160
AACTTTGGGA ATCCCCCCAA GAAATCTCCA GGCATCAAGC ACTGCGGTTAC AGTGTTATTA 2220
CGTTTATGAT CACAGCGGTG AAGCGGTTAA GGGAATCCAA GATGCTGACT CTATCATGGT 2280
TCAATCAGCC CTTGATGGTG ATAGCACCCT CTCAGGAGGA GACAATGAAT CTGAAACAG 2340
CGATGTGGAT ATTGGCGAAC CTGATACCGA GGATATGCT ATCACTGACC GGGGATCTGC 2400
TCCCATCTCT ATGGGGTTCA GGCTTCTGA TGTTGAAACT GCAGAAGGAG GGAGATCCA 2460
CGAGCTCCTG AGACTCCAAT CCAGAGGCAA CAACTTTCCG AAGCTTGGGA AAACTCTCAA 2520
TGTTCCTCCG CCCCGGACC CCGGTAGGGC CAGCACTTCC GGGACACCCA TTAAAAGGG 2580
CACACGACGCG AGATTAGCCT CATTTGGAAC GGAGATCGCG TCTTTATTGA CAGGTGGTGC 2640
AACCCAATGT GCTCGAAAGT CACCCTCGGA ACCATCAGGG CCAGGTGCAC CTGCGGGGAA 2700
TGTCCCCGAG TGTGTGAGCA ATGCCGCACT GATACAGGAG TGGACACCCG AATCTGGTAC 2760
CACAATCTCC CCGAGATCCC AGAATAATGA AGAAGGGGGA GACTATTATG ATGATGAGCT 2820
GTTCTCTGAT GTCCAAGATA TTAAAAACAGC CTTGGCCAAA ATACACGAGG ATAATCAGAA 2880
GATAATCTCC AAGCTAGAAT CACTGCTGTT ATTGAAGGGA GAAGTTGAGT CAATTAAGAA 2940
GCAGATCAAC AGGCAAAATA TCAGCATATC CACCCTGGAA GGACACCTCT CAAGCATCAT 3000
GATCGCCATT CCTGGACTTG GAAGGATCC CAACGACCCC ACTGCAGATG TCGAAATCAA 3060
```

FIG 5A

```
TCCCGACTTG AAACCCATCA TAGGCAGAGA TTCAGGCCGA GCACTGGCCG AAGTTCTCAA 3120
GAAACCCGTT GCCAGCCGAC AACTCCAAGG AATGACAAAT GGACGGACCA GTTCCAGAGG 3180
ACAGCTGCTG AAGGAATTTC AGCTAAAGCC GATCGGGAAA AAGATGAGCT CAGCCGTCGG 3240
GTTTGTTCCT GACACCGGCC CTGCATCACG CAGTGTAATC CGCTCCATTA TAAAATCCAG 3300
CCGGCTAGAG GAGGATCGGA AGCGTTACCT GATGACTCTC CTTGATGATA TCAAAGGAGC 3360
CAATGATCTT GCCAAGTTCC ACCAGATGCT GATGAAGATA ATAATGAAGT AGCTACAGCT 3420
CAACTTACCT GCCAACCCCA TGCCAGTCGA CCCAACTAGT ACAACCTAAA TCCATTATAA 3480
AAAACTTAGG AGCAAAGTGA TTGCCTCCCA AGGTCCACAA TGACAGAGAC CTACGACTTC 3540
GACAAGTCGG CATGGGACAT CAAAGGGTCG ATCGCTCCGA TACAACCCAC CACCTACAGT 3600
GATGGCAGGC TGGTGCCCCA GGTCAGAGTC ATAGATCCTG GTCTAGGCGA CAGGAAGGAT 3660
GAATGCTTTA TGTACATGTT TCTGCTGGGG GTTGTTGAGG ACAGCGATTC CCTAGGGCCT 3720
CCAATCGGGC GAGCATTTGG GTTCCTGCCC TTAGGTGTTG GCAGATCCAC AGCAAAGCCC 3780
GAAAAACTCC TCAAAGAGGC CACTGAGCTT GACATAGTTG TTAGACGTAC AGCAGGGCTC 3840
AATGAAAAAC TGGTGTTCTA CAACAACACC CCACTAACTC TCCTCACACC TTGGAGAAAG 3900
GTCCTAACAA CAGGGAGTGT CTTCAACGCA AACCAAGTGT GCAATGCGGT TAATCTGATA 3960
CCGCTCGATA CCCCGCCAGAG GTTCCGTGTT GTTTATATGA GCATCACCCG TCTTTCGGAT 4020
AACGGGTATT ACACCGTTCC TAGAAGAATG CTGGAATTCA GATCGGTCA TGCAGTGGCC 4080
TTCAACCTGC TGGTGACCCT TAGGATTGAC AAGGCGATAG GCCCTGGGAA GATCATCGAC 4140
AATACAGAGC AACTTCCTGA GGCAACATTT ATGGTCCACA TCGGGAACTT CAGGAGAAAG 4200
AAGAGTGAAG TCTACTCTGC CGATTATTGC AAAATGAAAA TCGAAAGAT GGGCCTGGTT 4260
TTTGCACTTG GTGGGATAGG GGGCACCAGT CTTCACATTA GAAGCACAGG CAAAATGAGC 4320
AAGACTCTCC ATGCACAACT CGGGTTCAAG AAGACCTTAT GTTACCCGCT GATGGATATC 4380
AATGAAGACC TTAATCGATT ACTCTGGAGG AGCAGATGCA AGATAGTAAG AATCCAGGCA 4440
GTTTTGCAGC CATCAGTTCC TCAAGAATTC CGCATTTACC ACGACGTGAT CATAAATGAT 4500
GACCAAGGAC TATTCAAAGT TCTGTAGACC GTAGTGCCCA GCAATGCCCG AAAACGACCC 4560
CCCTCACAAT GACAGCCAGA AGGCCCGGAC AAAAAGCCCC CCTCCGAAAG ACTCCACGGA 4620
CCAAGCGAGA GGCCAGCCAG CAGCCGACGG CAAGCGCGAA CACCAGGCGG CCCCAGCACA 4680
GAACAGCCCT GACACAAGGC CACCACCAGC CACCCCAATC TGCATCCTCC TCGTGGGACC 4740
CCCGAGGACC AACCCCCAAG GCTGCCCCCG ATCCAAACCA CCAACCGCAT CCCCACCACC 4800
CCCGGGAAAG AAACCCCCAG CAATTGGAAG GCCCCTCCCC CTCTTCCTCA ACACAAGAAC 4860
TCCACAACCG AACCGCACAA GCGACCGAGG TGACCCAACC GCAGGCATCC GACTCCCTAG 4920
ACAGATCCTC TCTCCCCGGC AAACTAAACA AAACTTAGGG CCAAGGAACA TACACACCCA 4980
ACAGAACCCA GACCCCGGCC CACGGCGCCG CGCCCCCAAC CCCCGACAAC CAGAGGGAGC 5040
CCCCAACCAA TCCCGCCGGC TCCCCGGTG CCCACAGGCA GGGACACCAA CCCCCGAACA 5100
GACCCAGCAC CCAACCATCG ACAATCCAAG ACGGGGGGC CCCCCAAAA AAAGGCCCCC 5160
AGGGGCCGAC AGCCAGCACC GCGAGGAAGC CCACCCACCC CACACACGAC CACGGCAACC 5220
AAACCAGAAC CCAGACCACC CTGGGCCACC AGCTCCAGA CTCGCCATC ACCCGCAGA 5280
AAGGAAAGGC CACAACCCGC GCACCCAGC CCCGATCCGG CGGGGAGCCA CCCAACCCGA 5340
ACCAGCACCC AAGAGCGATC CCCGAAGGAC CCCCGAACCG CAAAGGACAT CAGTATCCCA 5400
CAGCCTCTCC AAGTCCCCCG GTCTCCTCCT CTTCTCGAAG GGACCAAAAG ATCAATCCAC 5460
CACACCCGAC GACACTCAAC TCCCCACCCC TAAAGGAGAC ACCGGGAATC CCAGAATCAA 5520
GACTCATCCA ATGTCCATCA TGGGTCTCAA GGTGAACGTC TCTGCCATAT TCATGGCAGT 5580
ACTGTTAACT CTCCAAACAC CCACCGGTCA AATCCATTGG GGCAATCTCT CTAAGATAGG 5640
GGTGGTAGGA ATAGGAAGTG CAAGCTACAA AGTTATGACT CGTTCCAGCC ATCAATCATT 5700
AGTCATAAAA TTAATGCCCA ATATAACTCT CCTCAATAAC TGCACGAGGG TAGAGATTGC 5760
AGAATACAGG AGACTACTGA GAACAGTTTT GGAACCAATT AGAGATGCAC TTAATGCAAT 5820
GACCCAGAAT ATAAGACCGG TTCAGAGTGT AGCTTCAAGT AGGAGACACA ACAGATTTGC 5880
GGGAGTAGTC CTGGCAGGTG CGGCCCTAGG CGTTGCCACA GCTGCTCAGA TAACAGCCGG 5940
CATTGCACTT CACCAGTCCA TGCTGAACTC TCAAGCCATC GACAATCTGA GAGCGAGCCT 6000
GGAAACTACT AATCAGGCAA TTGAGACAAT CAGACAAGCA GGGCAGGAGA TGATATTGGC 6060
TGTTCAGGGT GTCCAAGACT ACATCAATAA TGAGCTGATA CCGTCTATGA ACCAACTATC 6120
TTGTGATTTA ATCGGCCAGA AGCTCGGGCT CAAATTGCTC AGATACTATA CAGAAATCCT 6180
```

FIG 5B

```
GTCATTATTT GGCCCCAGTT TACGGGACCC CATATCTGCG GAGATATCTA TCCAGGCTTT 6240
GAGCTATGCG CTTGGAGGAG ACATCAATAA GGTGTTAGAA AAGCTCGGAT ACAGTGGAGG 6300
TGATTTACTG GGCATCTTAG AGAGCGGAGG AATAAAGGCC CGGATAACTC ACGTCGACAC 6360
AGAGTCCTAC TTCATTGTCC TCAGTATAGC CTATCCGACG CTGTCCGAGA TTAAGGGGGT 6420
GATTGTCCAC CGGCTAGAGG GGGTCTCGTA CAACATAGGC TCTCAAGAGT GGTATACCAC 6480
TGTGCCCAAG TATGTTGCAA CCCAAGGGTA CCTTATCTCG AATTTTGATG AGTCATCGTG 6540
TACTTTCATG CCAGAGGGGA CTGTGTGCAG CCAAAATGCC TTGTACCCGA TGAGTCCTCT 6600
GCTCCAAGAA TGCCTCCGGG GGTACACCAA GTCCTGTGCT CGTACACTCG TATCCGGGTC 6660
TTTTGGGAAC CGGTTCATTT TATCACAAGG GAACCTAATA GCCAATTGTG CATCAATCCT 6720
TTGCAAGTGT TACACAACAG GAACGATCAT TAATCAAGAC CCTGACAAGA TCCTAACATA 6780
CATTGCTGCC GATCACTGCC CGGTAGTCGA GGTGAACGGC GTGACCATCC AAGTCGGGAG 6840
CAGGAGGTAT CCAGACGCTG TGTACTTGCA CAGAATTGAC CTCGGTCCTC CCATATCATT 6900
GGAGAGGTTG GACGTAGGGA CAAATCTGGG GAATGCAATT GCTAAGTTGG AGGATGCCAA 6960
GGAATTGTTG GAGTCATCGG ACCAGATATT GAGGAGTATG AAAGGTTTAT CGAGCACTAG 7020
CATAGTCTAC ATCCTGATTG CAGTGTGTCT TGGAGGGTTG ATAGGGATCC CCGCTTTAAT 7080
ATGTTGCTGC AGGGGGCGTT GTAACAAAAA GGGAGAACAA GTTGGTATGT CAAGACCAGG 7140
CCTAAAGCCT GATCTTACGG GAACATCAAA ATCCTATGTA AGGTCGCTCT GATCCTCTAC 7200
AACTCTTGAA ACACAAATGT CCCACAAGTC TCCTCTTCGT CATCAAGCAA CCACCGCACC 7260
CAGCATCAAG CCCACCTGAA ATTATCTCCG GCTTCCCTCT GGCCGAACAA TATCGGTAGT 7320
TAATCAAAAC TTAGGGTGCA AGATCATCCA CAATGTCACC ACAACGAGAC CGGATAAATG 7380
CCTTCTACAA AGATAACCCC CATCCCAAGG GAAGTAGGAT AGTCATTAAC AGAGAACATC 7440
TTATGATTGA TAGACCTTAT GTTTGCTGG CTGTTCTGTT TGTCATGTTT CTGAGCTTGA 7500
TCGGGTTGCT AGCCATTGCA GGCATTAGAC TTCATCGGGC AGCCATCTAC ACCGCAGAGA 7560
TCCATAAAAG CCTCAGCACC AATCTAGATG TAACTAACTC AATCGAGCAT CAGGTCAAGG 7620
ACGTGCTGAC ACCACTCTTC AAAATCATCG GTGATGAAGT GGGCCTGAGG ACACCTCAGA 7680
GATTCACTGA CCTAGTGAAA TTAATCTCTG ACAAGATTAA ATTCCTTAAT CCGGATAGGG 7740
AGTACGACTT CAGAGATCTC ACTTGGTGTA TCAACCCGCC AGAGAGAATC AAATTGGATT 7800
ATGATCAATA CTGTGCAGAT GTGGCTGCTG AAGAGCTCAT GAATGCATTG GTGAACTCAA 7860
CTCTACTGGA GACCAGAACA ACCAATCAGT TCCTAGCTGT CTCAAAGGGA AACTGCTCAG 7920
GGCCCACTAC AATCAGAGGT CAATTCTCAA ACATGTCGCT GTCCCTGTTA GACTTGTATT 7980
TAGGTCGAGG TTACAATGTG TCATCTATAG TCACTATGAC ATCCCAGGGA ATGTATGGGG 8040
GAACTTACCT AGTGGAAAAG CCTAATCTGA GCAGCAAAAG GTCAGAGTTG TCACAACTGA 8100
GCATGTACCG AGTGTTTGAA GTAGGTGTTA TCAGAAATCC GGGGTTGGGG GCTCCGGTGT 8160
TCCATATGAC AAAACTATCTT GAGCAACCAG TCAGTAATGA TCTCAGCAAC TGTATGGTGG 8220
CTTTGGGGGA GCTCAAACTC GCAGCCCTTT GTCACGGGGA AGATTCTATC ACAATTCCCT 8280
ATCAGGGATC AGGGAAAGGT GTCAGCTTCC AGCTCGTCAA GCTAGGTGTC TGGAAATCCC 8340
CAACCGACAT GCAATCCTGG GTCCCCTTAT CAACGGATGA TCCAGTGATA GACAGGCTTT 8400
ACCTCTCATC TCACAGAGGT GTTATCGCTG ACAATCAAGC AAAATGGGCT GTCCCGACAA 8460
CACGAACAGA TGACAAGTTG CGAATGGAGA CATGCTTCCA ACAGGCGTGT AAGGGTAAAA 8520
TCCAAGCACT CTGCGAGAAT CCCGAGTGGG CACCATTGAA GGATAACAGG ATTCCTTCAT 8580
ACGGGGTCTT GTCGTTGAT CTGAGTCTGA CAGTTGAGCT TAAAATCAAA ATTGCTTCGG 8640
GATTCGGGCC ATTGATCACA CACGGTTCAG GGATGGACCT ATACAAATCC AACCACAACA 8700
ATGTGTATTG GCTGACTATC CCGCCAATGA AGAACCTAGC CTTAGGTGTA ATCAACACAT 8760
TGGAGTGGAT ACCGAGATTC AAGGTTAGTC CCTACCTCTT CACTGTCCCA ATTAAGGAAG 8820
CAGGCGAAGA CTGCCATGCC CCAACATACC TACCTGCGGA GGTGGATGGT GATGTCAAAC 8880
TCAGTTCCAA TCTGGTGATT CTACCTGGTC AAGATCTCCA ATATGTTTTG GCAACCTACG 8940
ATACTTCCAG GGTTGAACAT GCTGTGGTTT ATTACGTTTA CAGCCCAAGC CGCTCATTTT 9000
CTTACTTTTA TCCTTTTAGG TTGCCTATAA AGGGGGTCCC CATCGAATTA CAAGTGGAAT 9060
GCTTCACATG GGACCAAAAA CTCTGGTGCC GTCACTTCTG TGTGCTTGCG GACTCAGAAT 9120
CTGGTGGACA TATCACTCAC TCTGGGATGG TGGGCATGGG AGTCAGCTGC ACAGTCACCC 9180
GGGAAGATGG AACCAATCGC AGATAGGGCT GCTAGTGAAC CAATCACATG ATGTCACCCA 9240
GACATCAGGC ATACCCACTA GTGTGAAATA GACATCAGAA TTAAGAAAAA CGTAGGGTCC 9300
```

FIG 5C

```
AAGTGGTTCC CCGTTATGGA CTCGCTATCT GTCAACCAGA TCTTATACCC TGAAGTTCAC 9360
CTAGATAGCC CGATAGTTAC CAATAAGATA GTAGCCATCC TGGAGTATGC TCGAGTCCCT 9420
CACGCTTACA GCCTGGAGGA CCCTACACTG TGTCAGAACA TCAAGCACCG CCTAAAAAAC 9480
GGATTTTCCA ACCAAATGAT TATAAACAAT GTGGAAGTTG GGAATGTCAT CAAGTCCAAG 9540
CTTAGGAGTT ATCCGGCCCA CTCTCATATT CCATATCCAA ATTGTAATCA GGATTTATTT 9600
AACATAGAAG ACAAAGAGTC AACGAGGAAG ATCCGTGAAC TCCTCAAAAA GGGGAATTCG 9660
CTGTACTCCA AAGTCAGTGA TAAGGTTTTC CAATGCTTAA GGGACACTAA CTCACGGCTT 9720
GGCCTAGGCT CCGAATTGAG GGAGGACATC AAGGAGAAAG TTATTAACTT GGGAGTTTAC 9780
ATGCACAGCT CCCAGTGGTT TGAGCCCTTT CTGTTTTGGT TTACAGTCAA GACTGAGATG 9840
AGGTCAGTGA TTAAATCACA AACCCATACT TGCCATAGGA GGAGACACAC ACCTGTATTC 9900
TTCACTGGTA GTTCAGTTGA GTTGCTAATC TCTCGTGACC TTGTTGCTAT AATCAGTAAA 9960
GAGTCTCAAC ATGTATATTA CCTGACATTT GAACTGGTTT TGATGTATTG TGATGTCATA 10020
GAGGGGAGGT TAATGACAGA GACCGCTATG ACTATTGATG CTAGGTATAC AGAGCTTCTA 10080
GGAAGAGTCA GATACATGTG GAAACTGATA GATGGTTTCT TCCCTGCACT CGGGAATCCA 10140
ACTTATCAAA TTGTAGCCAT GCTGGAGCCT CTTTCACTTG CTTACCTGCA GCTGAGGGAT 10200
ATAACAGTAG AACTCAGAGC TGCTTTCCTT AACCACTGCT TTACTGAAAT ACATGATGTT 10260
CTTGACCAAA ACGGGTTTTC TGATGAAGGT ACTTATCATG AGTTAACTGA AGCTCTAGAT 10320
TACATTTTCA TAACTGATGA CATACATCTG ACAGGGGAGA TTTTCTCATT TTTCAGAAGT 10380
TTCGGCCACC CCAGACTTGA AGCAGTAACG GCTGCTGAAA ATGTTAGGAA ATACATGAAT 10440
CAGCCTAAAG TCATTGTGTA TGAGACTCTG ATGAAGGTC ATGCCATATT TTGTGGAATC 10500
ATAATCAACG GCTATCGTGA CAGGCACGGA GGCAGTTGGC CACCGCTGAC CCTCCCCCTG 10560
CATGCTGCAG ACACAATCCG GAATGCTCAA GCTTCAGGTG AAGGGTTAAC ACATGAGCAG 10620
TGCGTTGATA ACTGGAAATC TTTTGCTGGA GTGAAATTTG GCTGCTTTAT GCCTCTTAGC 10680
CTGGATAGTG ATCTGACAAT GTACCTAAAG GACAAGGCAC TTGCTGCTCT CCAAAGGGAA 10740
TGGGATTCAG TTTACCCGAA AGAGTTCCTG CGTTACGACC CTCCCAAGGG AACCGGGTCA 10800
CGGAGGCTTG TAGATGTTTT CCTTAATGAT TCGAGCTTTG ACCCATATGA TGTGATAATG 10860
TATGTTGTAA GTGGAGCTTA CCTCCATGAC CCTGAGTTCA ACCTGTCTTA CAGCCTGAAA 10920
GAAAAGGAGA TCAAGGAAAC AGGTAGACTT TTTGCTAAAA TGACTTACAA AATGAGGGCA 10980
TGCCAAGTGA TTGCTGAAAA TCTAATCTCA AACGGGATTG GCAAATATTT TAAGGACAAT 11040
GGGATGGCCA AGGATGAGCA CGATTTGACT AAGGCACTCC ACACTCTAGC TGTCTCAGGA 11100
GTCCCAAAAG ATCTCAAAGA AAGTCACAGG GGGGGCCAG TCTTAAAAAC CTACTCCGA 11160
AGCCCAGTCC ACACAAGTAC CAGGAACGTG AGAGCAGCAA AAGGGTTTAT AGGGTTCCCT 11220
CAAGTAATTC GGCAGGACCA AGACACTGAT CATCCGGAGA ATATGGAAGC TTACGAGACA 11280
GTCAGTGCAT TTATCACGAC TGATCTCAAG AAGTACTGCC TTAATTGGAG ATATGAGACC 11340
ATCAGCTTGT TTGCACAGAG GCTAAATGAG ATTTACGGAT TGCCCTCATT TTTCCAGTGG 11400
CTGCATAAGA GGCTTGAGAC CTCTGTCCTG TATGTAAGTG ACCCTCATTG CCCCCCCGAC 11460
CTTGACGCCC ATATCCCGTT ATATAAAGTC CCCAATGATC AAATCTTCAT TAAGTACCCT 11520
ATGGGAGGTA TAGAAGGGTA TTGTCAGAAG CTGTGGACCA TCAGCACCAT TCCCTATCTA 11580
TACCTGGCTG CTTATGAAGA CGGAGTAAGG ATTGCTTCGT TAGTGCAAGG GGACAATCAG 11640
ACCATAGCCG TAACAAAAAG GGTACCCAGC ACATGGCCCT ACAACCTTAA GAAACGGGAA 11700
GCTGCTAGAG TAACTAGAGA TTACTTTGTA ATTCTTAGGC AAAGGCTACA TGATATTGGC 11760
CATCACCTCA AGGCAAATGA GACAATTGTT TCATCACATT TTTTTGTCTA TTCAAAAGGA 11820
ATATATTATG ATGGGCTACT TGTGTCCCAA TCACTCAAGA GCATCGCAAG ATGTGTATTC 11880
TGGTCAGAGA CTATAGTTGA TGAAACAAGG GCAGCATGCA GTAATATTGC TACAACAATG 11940
GCTAAAAGCA TCGAGAGAGG TTATGACCGT TACCTGCAT ATTCCCTGAA CGTCCTAAAA 12000
GTGATACAGC AAATTCTGAT CTCTCTTGGC TTCACAATCA ATTCAACCAT GACCCGGGAT 12060
GTAGTCATAC CCCTCCTCAC AAACAACGAC CTCTTAATAA GGATGGCACT GTTGCCCGCT 12120
CCTATTGGGG GGATGAATTA TCTGAATATG AGCAGGCTGT TGTCAGAAA CATCGGTGAT 12180
CCAGTAACAT CATCAATTGC TGATCTCAAG AGAATGATTC TCGCCTCACT AATGCCTGAA 12240
GAGACCCTCC ATCAAGTAAT GACACAACAA CCGGGGGACT CTTCATTCCT AGACTGGGCT 12300
AGCGACCCTT ACTCAGCAAA TCTTGTATGT GTCCAGAGCA TCACTAGACT CCTCAAGAAC 12360
ATAACTGCAA CGTTTGTCCT GATCCATAGT CCAAACCCAA TGTTAAAAGG ATTATTCCAT 12420
```

FIG 5D

```
GATGACAGTA AAGAAGAGGA CGAGGGACTG GCGGCATTCC TCATGGACAG GCATATTATA 12480
GTACCTAGGG CAGCTCATGA AATCCTGGAT CATAGTGTCA CAGGGGCAAG AGAGTCTATT 12540
GCAGGCATGC TGGATACCAC AAAAGGCTTG ATTCGAGCCA GCATGAGGAA GGGGGGGTTA 12600
ACCTCTCGAG TGATAACCAG ATTGTCCAAT TATGACTATG AACAATTCAG AGCAGGGATG 12660
GTGCTATTGA CAGGAAGAAA GAGAAATGTC CTCATTGACA AAGAGTCATG TTCAGTGCAG 12720
CTGGCGAGAG CTCTAAGAAG CCATATGTGG GCGAGGCTAG CTCGAGGACG GCCTATTTAC 12780
GGCCTTGAGG TCCCTGATGT ACTAGAATCT ATGCGAGGCC ACCTTATTCG GCGTCATGAG 12840
ACATGTGTCA TCTGCGAGTG TGGATCAGTC AACTACGGAT GGTTTTTTGT CCCCTCGGGT 12900
TGCCAACTGG ATGATATTGA CAAGGAAACA TCATCCTTGA GAGTCCCATA TATTGGTTCT 12960
ACCACTGATG AGAGAACAGA CATGAAGCTT GCCTTCGTAA GAGCCCAAG TCGATCCTTG 13020
CGATCTGCTG TTAGAATAGC AACAGTGTAC TCATGGGCTT ACGGTGATGA TGATAGCTCT 13080
TGGAACGAAG CCTGGTTGTT GGCTAGGCAA AGGGCCAATG TGAGCCTGGA GGAGCTAAGG 13140
GTGATCACTC CCATCTCAAC TTCGACTAAT TTAGCGCATA GGTTGAGGGA TCGTAGCACT 13200
CAAGTGAAAT ACTCAGGTAC ATCCCTTGTC CGAGTGGCGA GGTATACCAC AATCTCCAAC 13260
GACAATCTCT CATTTGTCAT ATCAGATAAG AAGGTTGATA CTAACTTTAT ATACCAACAA 13320
GGAATGCTTC TAGGGTTGGG TGTTTTAGAA ACATTGTTTC GACTCGAGAA AGATACCGGA 13380
TCATCTAACA CGGTATTACA TCTTCACGTC GAAACAGATT GTTGCGTGAT CCCGATGATA 13440
GATCATCCCA GGATACCCAG CTCCCGCAA CTAGAGCTGA GGGCAGAGCT ATGTACCAAC 13500
CCATTGATAT ATGATAATGC ACCTTTAATT GACAGAGATG CAACAAGGCT ATACACCCAG 13560
AGCCATAGGA GGCACCTTGT GGAATTTGTT ACATGGTCCA CACCCCAACT ATATCACATT 13620
TTAGCTAAGT CCACAGCACT ATCTATGATT GACCTGGTAA CAAAATTTGA GAAGGACCAT 13680
ATGAATGAAA TTTCAGCTCT CATAGGGGAT GACGATATCA ATAGTTTCAT AACTGAGTTT 13740
CTGCTCATAG AGCCAAGATT ATTCACTATC TACTTGGGCC AGTGTGCGGC CATCAATTGG 13800
GCATTTGATG TACATTATCA TAGACCATCA GGGAAATATC AGATGGGTGA GCTGTTGTCA 13860
TCGTTCCTTT CTAGAATGAG CAAAGGAGTG TTTAAGGTGC TTGTCAATGC TCTAAGCCAC 13920
CCAAAGATCT ACAAGAAATT CTGGCATTGT GGTATTATAG AGCCTATCCA TGTCCTTCA 13980
CTTGATGCTC AAAACTTGCA CACAACTGTG TGCAACATGG TTTACACATG CTATATGACC 14040
TACCTCGACC TGTTGTTGAA TGAAGAGTTA GAAGAGTTCA CATTTCTCTT GTGTGAAAGC 14100
GACGAGGATG TAGTACCGGA CAGATTCGAC AACATCCAGG CAAAACACTT ATGTGTTCTG 14160
GCAGATTTGT ACTGTCAACC AGGGACCTGC CCACCAATTC GAGGTCTAAG ACCGGTAGAG 14220
AAATGTGCAG TTCTAACCGA CCATATCAAG GCAGAGGCTA TGTTATCTCC AGCAGGATCT 14280
TCGTGGAACA TAAATCAAT TATTGTAGAC CATTACTCAT GCTCTCTGAC TTATCTCCGG 14340
CGAGGATCGA TCAAACAGAT AAGATTGAGA GTTGATCCAG GATTCATTTT CGACGCCCTC 14400
GCTGAGGTAA ATGTCAGTCA GCCAAAGATC GGCAGCAACA ACATCTCAAA TATGAGCATC 14460
AAGGCTTTCA GACCCCCACA CGATGATGTT GCAAAATTGC TCAAAGATAT CAACACAAGC 14520
AAGCACAATC TTCCCATTTC AGGGGGCAAT CTCGCCAATT ATGAAATCCA TGCTTTCCGC 14580
AGAATCGGGT TGAACTCATC TGCTTGCTAC AAAGCTGTTG AGATATCAAC ATTAATTAGG 14640
AGATGCCTTG AGCCAGGGGA GGACGGCTTG TTCTTGGGTG AGGGATCGGG TTCTATGTTG 14700
ATCACTTATA AAGAGATACT TAAACTAAAC AAGTGCTTCT ATAATAGTGG GGTTTCCGCC 14760
AATTCTAGAT CTGGTCAAAG GGAATTAGCA CCCTATCCCT CCGAAGTTGG CCTTGTCGAA 14820
CACAGAATGG GAGTAGGTAA TATTGTCAAA GTGCTCTTTA ACGGGAGGCC CGAAGTCACG 14880
TGGGTAGGCA GTGTAGATTG CTTCAATTTC ATAGTTAGTA ATATCCCTAC CTCTAGTGTG 14940
GGGTTTATCC ATTCAGATAT AGAGACCTTG CCTGACAAAG ATACTATAGA GAAGCTAGAG 15000
GAATTGGCAG CCATCTTATC GATGGCTCTG CTCCTGGGCA AAATAGGATC AATACTGGTG 15060
ATTAAGCTTA TGCCTTTCAG CGGGGATTTT GTTCAGGGAT TTATAAGTTA TGTAGGGTCT 15120
CATTATAGAG AAGTGAACCT TGTATACCCT AGATACAGCA ACTTCATCTC TACTGAATCT 15180
TATTTGGTTA TGACAGATCT CAAGGCTAAC CGGCTAATGA ATCCTGAAAA GATTAAGCAG 15240
CAGATAATTG AATCATCTGT GAGGACTTCA CCTGGACTTA TAGGTCACAT CCTATCCATT 15300
AAGCAACTAA GCTGCATACA AGCAATGTG GGAGACGCAG TTAGTAGAGG TGATATCAAT 15360
CCTACTCTGA AAAACTTAC ACCTATAGAG CAGGTGCTGA TCAATTGCGG GTTGCAATT 15420
AACGGACCTA AGCTGTGCAA AGAATTGATC CACCATGATG TTGCCTCAGG GCAAGATGGA 15480
TTGCTTAATT CTATACTCAT CCTCTACAGG GAGTTGGCAA GATTCAAAGA CAACCAAAGA 15540
```

FIG 5E

```
AGTCAACAAG GGATGTTCCA CGCTTACCCC GTATTGGTAA GTAGCAGGCA ACGAGAACTT 15600
ATATCTAGGA TCACCCGCAA ATTCTGGGGG CACATTCTTC TTTACTCCGG GAACAAAAAG 15660
TTGATAAATA AGTTTATCCA GAATCTCAAG TCCGGCTATC TGATACTAGA CTTACACCAG 15720
AATATCTTCG TTAAGAATCT ATCCAAGTCA GAGAAACAGA TTATTATGAC GGGGGGTTTG 15780
AAACGTGAGT GGGTTTTTAA GGTAACAGTC AAGGAGACCA AGAATGGTA TAAGTTAGTC 15840
GGATACAGTG CCCTGATTAA GGACTAATTG GTTGAACTCC GGAACCCTAA TCCTGCCCTA 15900
GGTGGTTAGG CATTATTTGC AATATATTAA AGAAAACTTT GAAAATACGA AGTTTCTATT 15960
CCCAGCTTTG TCTGGTGGCC GGCATGGTCC CAGCCTCCTC GCTGGCGCCG GCTGGGCAAC 16020
ATTCCGAGGG GACCGTCCCC TCGGTAATGG CGAATGGGAC GCGGCCGATC CGGCTGCTAA 16080
CAAAGCCCGA AGGAAGCTG AGTTGGCTGC TGCCACCGCT GAGCAATAAC TAGCATAACC 16140
CCTTGGGGCC TCTAAACGGG TCTTGAGGGG TTTTTGCTG AAAGGAGGAA CTATATCCGG 16200
ATGCGGCCGC GGGCCCTATG GTACCCAGCT TTTGTTCCCT TTAGTGAGGG TTAATTCCGA 16260
GCTTGGCGTA ATCATGGTCA TAGCTGTTTC CTGTGTGAAA TTGTTATCCG CTCACAATTC 16320
CACACAACAT AGGAGCCGGA AGCATAAAGT GTAAAGCCTG GGGTGCCTAA TGAGTGAGGT 16380
AACTCACATT AATTGCGTTG CGCTCACTGC CCGCTTTCCA GTCGGGAAAC CTGTCGTGCC 16440
AGCTGCATTA ATGAATCGGC CAACGCGCGG GGAGAGGCGG TTTGCGTATT GGGCGCTCTT 16500
CCGCTTCCTC GCTCACTGAC TCGCTGCGCT CGGTCGTTCG GCTGCGGCGA GCGGTATCAG 16560
CTCACTCAAA GGCGGTAATA CGGTTATCCA CAGAATCAGG GGATAACGCA GGAAAGAACA 16620
TGTGAGCAAA AGGCCAGCAA AAGGCCAGGA ACCGTAAAAA GGCCGCGTTG CTGGCGTTTT 16680
TCCATAGGCT CGGCCCCCCT GACGAGCATC ACAAAAATCG ACGCTCAAGT CAGAGGTGGC 16740
GAAACCCGAC AGGACTATAA AGATACCAGG CGTTCCCCCC TGGAAGCTCC CTCGTGCGCT 16800
CTCCTGTTCC GACCCTGCCG CTTACCGGAT ACCTGTCCGC CTTTCTCCCT TCGGGAAGCG 16860
TGGCGCTTTC TCAATGCTCA CGCTGTAGGT ATCTCAGTTC GGTGTAGGTC GTTCGCTCCA 16920
AGCTGGGCTG TGTGCACGAA CCCCCCGTTC AGCCCGACCG CTGCGCCTTA TCCGGTAACT 16980
ATCGTCTTGA GTCCAACCCG GTAAGACACG ACTTATCGCC ACTGGCAGCA GCCACTGGTA 17040
ACAGGATTAG CAGAGCGAGG TATGTAGGCG GTGCTACAGA GTTCTTGAAG TGGTGGCCTA 17100
ACTACGGCTA CACTAGAAGG ACAGTATTTG GTATCTGCGC TCTGCTGAAG CCAGTTACCT 17160
TCGGAAAAAG AGTTGGTAGC TCTTGATCCG GCAAACAAAC CACCGCTGGT AGCGGTGGTT 17220
TTTTTGTTTG CAAGCAGCAG ATTACGCGCA GAAAAAAAGG ATCTCAAGAA GATCCTTTGA 17280
TCTTTTCTAC GGGGTCTGAC GCTCAGTGGA ACGAAAACTC ACGTTAAGGG ATTTTGGTCA 17340
TGAGATTATC AAAAAGGATC TTCACCTAGA TCCTTTTAAA TTAAAAATGA AGTTTTAAAT 17400
CAATCTAAAG TATATATGAG TAAACTTGGT CTGACAGTTA CCAATGCTTA ATCAGTGAGG 17460
CACCTATCTC AGCGATCTGT CTATTTCGTT CATCCATAGT TGCCTGACTG CCCGTCGTGT 17520
AGATAACTAC GATACGGGAG GGCTTACCAT CTGGCCCCAG TGCTGCAATG ATACCGCGAG 17580
ACCCACGCTC ACCGGCTCCA GATTTATCAG CAATAAACCA GCCAGCCGGA AGGGCCGAGC 17640
GCAGAAGTGG TCCTGCAACT TTATCCGCCT CCATCCAGTC TATTAATTGT TGCCGGGAAG 17700
CTAGAGTAAG TAGTTCGCCA GTTAATAGTT TGCGCAACGT TGTTGCCATT GCTACAGGCA 17760
TCGTGGTGTC ACGCTCGTCG TTTGGTATGG CTTCATTCAG CTCCGGTTCC CAACGATCAA 17820
GGCGAGTTAC ATGATCCCCC ATGTTGTGAA AAAAGCGGT TAGCTCCTTC GGTCCTCCGA 17880
TCGTTGTCAG AAGTAAGTTG GCCGCAGTGT TATCACTCAT GCTTATGGCA GCACTGCATA 17940
ATTCTCTTAC TGTCATGCCA TCCGTAAGAT GCTTTTCTGT GACTGGTGAG TACTCAACCA 18000
AGTCATTCTG AGAATAGTGT ATGCGGCGAC CGAGTTGCTC TTGCCCGGCG TCAATACGGG 18060
ATAATACCGC GCCACATAGC AGAACTTTAA AAGTGCTCAT CATTGGAAAA CGTTCTTCGG 18120
GGCGAAAACT CTCAAGGATC TTACCGCTGT TGAGATCCAG TTCGATGTAA CCCACTCGTG 18180
CACCCAACTG ATCTTCAGCA TCTTTTACTT TCACCAGCGT TTCTGGGTGA GCAAAAACAG 18240
GAAGGCAAAA TGCCGCAAAA AAGGGAATAA GGGCGACACG GAAATGTTGA ATACTCATAC 18300
TCTTCCTTTT TCAATATTAT TGAAGCATTT ATCAGGGTTA TTGTCTCATG AGCGGATACA 18360
TATTTGAATG TATTTAGAAA AATAAACAAA TAGGGGTTCC GCGCACATTT CCCCGAAAAG 18420
TGCCACCTGA AATTGTAAAC GTTAATATTT TGTTAAAATT CGCGTTAAAT TTTTGTTAAA 18480
TCAGCTCATT TTTTAACCAA TAGGCCGAAA TCGGCAAAAT CCCTTATAAA TCAAAAGAAT 18540
AGACCGAGAT AGGGTTGAGT GTTGTTCCAG TTTGGAACAA GAGTCCACTA TTAAAGAACG 18600
TGGACTCCAA CGTCAAAGGG CGAAAAACCG TCTATCAGGG CGATGGCCCA CTACGTGAAC 18660
```

FIG 5F

```
CATCACCCTA ATCAAGTTTT TTGGGGTCGA GGTGCCGTAA AGCACTAAAT CGGAACCCTA 18720
AAGGGAGCCC CCGATTTAGA GCTTGACGGG GAAAGCCGGC GAACGTGGCG AGAAAGGAAG 18780
GGAAGAAAGC GAAAGGAGCG GGCGCTAGGG CGCTGGCAAG TGTAGCGGTC ACGCTGCGCG 18840
TAACCACCAC ACCCGCCCGC CTTAATGCGC CGCTACAGGG CGCGTCCCAT TCGCCATTCA 18900
GGCTGCGCGA CTGTTGGGAA GGGCGATCGG TGCGGGCCTC TTCGCTATTA CGCCAGCCAC 18960
CGCGGTG                                                         18967
```

*FIG 5G*

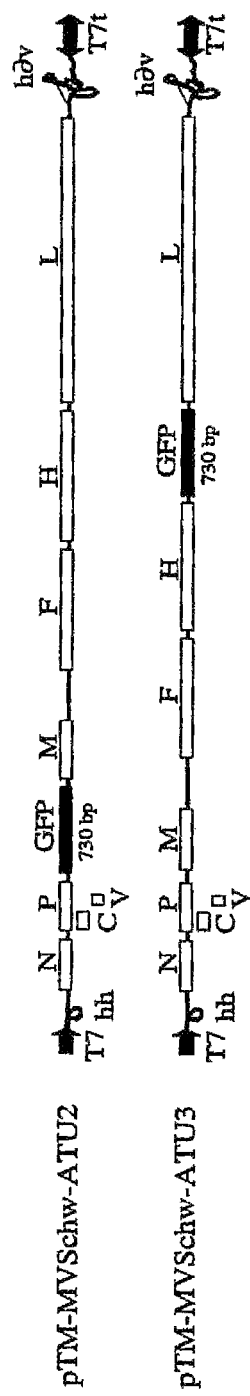
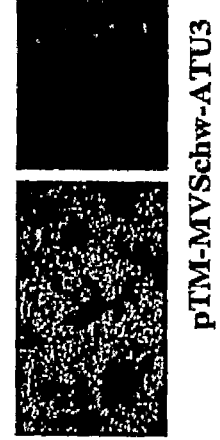
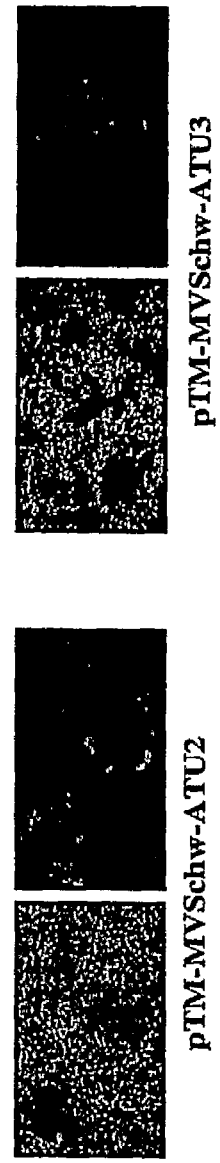
FIG 10A
FIG 10B

SEQUENCE LISTING

<160> NUMBER OF SEQ ID NOS: 91

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atccgagatg gccacacttt                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaagtgtggc catctcggat                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgattctggg taccatccta                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taggatggta cccagaatca                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tatgccatgg gagtaggagt                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
actcctactc ccatggcata                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tggcaggaat ctcggaagaa                                          20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttcttccgag attcctgcca                                          20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcatcaagca ctgggttaca                                          20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgtaacccag tgcttgatgc                                          20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tacaggagtg gacacccgaa                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttcgggtgtc cactcctgta                                          20

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aggacagctg ctgaaggaat                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
attccttcag cagctgtcct                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttgttgagga cagcgattcc                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaatcgctg tcctcaacaa                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agagtgaagt ctactctgcc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggcagagtag acttcactct                                              20
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgacacaagg ccaccaccag                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctggtggtgg ccttgtgtca                                                 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agctcccaga ctcggccatc                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatggccgag tctgggagct                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccagccatca atcattagtc                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gactaatgat tgatggctgg                                                 20

<210> SEQ ID NO 25
```

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agtttacggg accccatatc                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatatggggt cccgtaaact                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggaacctaat agccaattgt                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
acaattggct attaggttcc                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctcttcgtca tcaagcaacc                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggttgcttga tgacgaagag                                                 20

<210> SEQ ID NO 31
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tcacttggtg tatcaacccg                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgggttgata caccaagtga                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aactgtatgg tggctttggg                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cccaaagcca ccatacagtt                                                   20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgtgtattgg ctgactatcc                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggatagtcag ccaatacaca                                                   20

<210> SEQ ID NO 37
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 37
atcaggcata cccactagtg                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cactagtggg tatgcctgat                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcacagctcc cagtggtttg                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caaaccactg ggagctgtgc                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcatgagtta actgaagctc                                                   20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gagcttcagt taactcatga                                                   20

<210> SEQ ID NO 43
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 43
gtcacggagg cttgtagatg                                                     20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
catctacaag cctccgtgac                                                     20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtactgcctt aattggagat                                                     20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
atctccaatt aaggcagtac                                                     20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgatgggcta cttgtgtccc                                                     20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gggacacaag tagcccatca                                                     20

<210> SEQ ID NO 49
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 49
acccttactc agcaaatctt                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aagatttgct gagtaagggt                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tctatgcgag gccaccttat                                                    20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ataaggtggc ctcgcataga                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ttgtccgagt ggcgaggtat                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atacctcgcc actcggacaa                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
caattgggca tttgatgtac                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gtacatcaaa tgcccaattg                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gaggctatgt tatctccagc                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gctggagata acatagcctc                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agttggcctt gtcgaacaca                                               20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgtgttcgac aaggccaact                                               20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 61
ctggacttat aggtcacatc                                                  20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gatgtgacct ataagtccag                                                  20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggtttgaaac gtgagtgggt                                                  20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
acccactcac gtttcaaacc                                                  20

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
accaaacaaa gttgggtaag gatagttcaa tc                                    32

<210> SEQ ID NO 66
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tatgcggccg ctaatacgac tcactatagg gccaactttg tttggtctga                 50

<210> SEQ ID NO 67
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 67
ggtgacccgg gactccgggt tcgtcctca cggactcatc agaccaaaca         50

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gagtcccggg tcaccaaaca aagttgggta ag                           32

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggtttgtcct tgtttctttt                                         20

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
accaaacaaa gttgggtaag gatagttcaa tc                           32

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
attcccttaa ccgcttcacc                                         20

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctatggcagc atggtcagaa ata                                     23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
attgtcgatg gttgggtgct                                               20

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aaacttaggg ccaaggaaca tac                                           23

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggaccctacg tttttcttaa ttctg                                         25

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agatagggct gctagtgaac caat                                          24

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atcagcacct gctctatagg tgtaa                                         25

<210> SEQ ID NO 78
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcagcagata attgaatcat ctgtgaggac ttcac                              35

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cccggagtaa agaagaatgt gcccccagaa tttgc 35

<210> SEQ ID NO 80
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggcacattct tctttactcc gggaacaaaa agttg 35

<210> SEQ ID NO 81
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
atagggcccg cggccgcatc cggatatagt tcctcctttc a 41

<210> SEQ ID NO 82
<211> LENGTH: 18967
<212> TYPE: DNA
<213> ORGANISM: Artificial Sequence
<220> FEATURE:
<223> OTHER INFORMATION: Description of Artificial Sequence: Complete
      nucleotide sequence of the pTM-MVSChw plasmid (CNCM I-2889)

<400> SEQUENCE: 82
gcggccgcta atacgactca ctatagggcc aactttgttt ggtctgatga gtccgtgagg    60
acgaaacccg gagtcccggg tcaccaaaca aagttgggta aggatagttc aatcaatgat   120
catcttctag tgcacttagg attcaagatc ctattatcag ggacaagagc aggattaggg   180
atatccgaga tggccacact tttaaggagc ttagcattgt tcaaaagaaa caaggacaaa   240
ccacccatta catcaggatc cggtggagcc atcagaggaa tcaaacacat tattatagta   300
ccaatccctg gagattcctc aattaccact cgatccagac ttctggaccg gttggtgagg   360
ttaattggaa accggatgt gagcgggccc aaactaacag gggcactaat aggtatatta   420
tcctatttg tggagtctcc aggtcaattg attcagagga tcaccgatga ccctgacgtt   480
agcataaggc tgttagaggt tgtccagagt gaccagtcac aatctggcct taccttcgca   540
tcaagaggta ccaacatgga ggatgaggcg accaatactt ttcacatga tgatccaatt   600
agtagtgatc aatccaggtt cggatggttc gggaacaagg aaatctcaga tattgaagtg   660
caagacctg agggattcaa catgattctg ggtaccatcc tagcccaaat ttgggtcttg   720
ctcgcaaagg cggttacggc cccagacacg gcagctgatt cggagctaag aaggtggata   780
aagtacaccc aacaaagaag ggtagttggt gaatttagat tggagagaaa atggttggat   840
gtggtgagga acaggattgc cgaggacctc tccttacgcc gattcatggt cgctctaatc   900
ctggatatca agaacacc cggaaacaaa cccaggattg ctgaaatgat atgtgacatt   960
gatacatata tcgtagaggc aggattagcc agttttatcc tgactattaa gtttgggata   1020
gaaactatgt atcctgctct tggactgcat gaatttgctg gtgagttatc cacacttgag   1080
tccttgatga accttaccca gcaaatgggg gaaactgcac cctacatggt aatcctggag   1140
aactcaattc agaacaagtt cagtgcagga tcataccctc tgctctggag ctatgccatg   1200

```
ggagtaggag tggaacttga aaactccatg ggaggtttga actttggccg atcttacttt    1260
gatccagcat attttagatt agggcaagag atggtaagga ggtcagctgg aaaggtcagt    1320
tccacattgg catctgaact cggtatcact gccgaggatg caaggcttgt ttcagagatt    1380
gcaatgcata ctactgagga caagatcagt agagcggttg acccagaca agcccaagta    1440
tcatttctac acggtgatca aagtgagaat gagctaccga gattggggg caaggaagat     1500
aggagggtca aacagagtcg aggagaagcc agggagagct acagagaaac cgggcccagc    1560
agagcaagtg atgcgagagc tgcccatctt ccaaccggca caccctaga cattgacact     1620
gcaacggagt ccagccaaga tccgcaggac agtcgaaggt cagctgacgc cctgcttagg    1680
ctgcaagcca tggcaggaat ctcggaagaa caaggctcag acacggacac ccctatagtg    1740
tacaatgaca gaaatcttct agactaggtg cgagaggccg agggccagaa caacatccgc    1800
ctaccatcca tcattgttat aaaaaactta ggaaccaggt ccacacagcc gccagcccat    1860
caaccatcca ctcccacgat ggagccaat ggcagaagag caggcacgcc atgtcaaaaa     1920
cggactggaa tgcatccggg ctctcaaggc cgagcccatc ggctcactgg ccatcgagga    1980
agctatggca gcatggtcag aaatatcaga acccagga caggagcgag ccacctgcag      2040
ggaagagaag gcaggcagtt cgggtctcag caaaccatgc ctctcagcaa ttggatcaac    2100
tgaaggcggt gcacctcgca tccgcggtca gggacctgga gagagcgatg acgacgctga    2160
aactttggga atcccccaa gaaatctcca ggcatcaagc actgggttac agtgttatta     2220
cgtttatgat cacagcggtg aagcggttaa gggaatccaa gatgctgact ctatcatggt    2280
tcaatcaggc cttgatggtg atagcaccct ctcaggagga caatgaat ctgaaaacag      2340
cgatgtggat attggcgaac ctgataccga gggatatgct atcactgacc ggggatctgc    2400
tcccatctct atggggttca gggcttctga tgttgaaact gcagaaggag gggagatcca    2460
cgagctcctg agactccaat ccagaggcaa caactttccg aagcttggga aaactctcaa    2520
tgttcctccg cccccggacc ccggtagggc cagcacttcc gggacaccca ttaaaaaggg    2580
cacagacgcg agattagcct catttggaac ggagatcgcg tctttattga caggtggtgc    2640
aacccaatgt gctcgaaagt cacccctcgga accatcaggg ccaggtgcac ctgcggggaa   2700
tgtccccgag tgtgtgagca atgccgcact gatacaggag tggacacccg aatctggtac    2760
cacaatctcc ccgagatccc agaataatga agaaggggga gactattatg atgatgagct    2820
gttctctgat gtccaagata ttaaaacagc cttggccaaa atacacgagg ataatcagaa    2880
gataatctcc aagctagaat cactgctgtt attgaaggga gaagttgagt caattaagaa    2940
gcagatcaac aggcaaaata tcagcatatc caccctggaa ggacacctct caagcatcat    3000
gatcgccatt cctggacttg ggaaggatcc caacgacccc actgcagatg tcgaaatcaa    3060
tcccgacttg aaacccatca taggcagaga ttcaggccga gcactggccg aagttctcaa    3120
gaaacccgtt gccagccgac aactccaagg aatgacaaat ggacggacca gttccagagg    3180
acagctgctg aaggaatttc agctaaagcc gatcgggaaa aagatgagct cagccgtcgg    3240
gtttgttcct gacaccggcc ctgcatcacg cagtgtaatc cgctccatta taaaatccag    3300
ccggctagag gaggatcgga agcgttacct gatgactctc cttgatgata tcaaaggagc    3360
caatgatctt gccaagttcc accagatgct gatgaagata taatgaagt agctacagct    3420
caacttacct gccaacccca tgccagtcga cccaactagt acaacctaaa tccattataa    3480
aaaacttagg agcaaagtga ttgcctccca aggtccacaa tgacagagac ctacgacttc    3540
gacaagtcgg catgggacat caaagggtcg atcgctccga tacaacccac cacctacagt    3600
```

```
gatggcaggc tggtgcccca ggtcagagtc atagatcctg gtctaggcga caggaaggat    3660
gaatgcttta tgtacatgtt tctgctgggg gttgttgagg acagcgattc cctagggcct    3720
ccaatcgggc gagcatttgg gttcctgccc ttaggtgttg gcagatccac agcaaagccc    3780
gaaaaactcc tcaaagaggc cactgagctt gacatagttg ttagacgtac agcagggctc    3840
aatgaaaaac tggtgttcta caacaacacc ccactaactc tcctcacacc ttggagaaag    3900
gtcctaacaa cagggagtgt cttcaacgca aaccaagtgt gcaatgcggt taatctgata    3960
ccgctcgata ccccgcagag gttccgtgtt gtttatatga gcatcacccg tctttcggat    4020
aacgggtatt acaccgttcc tagaagaatg ctggaattca gatcggtcaa tgcagtggcc    4080
ttcaacctgc tggtgaccct taggattgac aaggcgatag gccctgggaa gatcatcgac    4140
aatacagagc aacttcctga ggcaacattt atggtccaca tcgggaactt caggagaaag    4200
aagagtgaag tctactctgc cgattattgc aaaatgaaaa tcgaaaagat gggcctggtt    4260
tttgcacttg gtgggatagg gggcaccagt cttcacatta gaagcacagg caaaatgagc    4320
aagactctcc atgcacaact cgggttcaag aagaccttat gttacccgct gatggatatc    4380
aatgaagacc ttaatcgatt actctggagg agcagatgca agatagtaag aatccaggca    4440
gttttgcagc catcagttcc tcaagaattc cgcatttacg acgacgtgat cataaatgat    4500
gaccaaggac tattcaaagt tctgtagacc gtagtgccca gcaatgcccg aaaacgaccc    4560
ccctcacaat gacagccaga aggcccggac aaaaagcccc cctccgaaag actccacgga    4620
ccaagcgaga ggccagccag cagccgacgg caagcgcgaa caccaggcgg ccccagcaca    4680
gaacagccct gacacaaggc caccaccagc cacccccaatc tgcatcctcc tcgtgggacc    4740
cccgaggacc aaccccccaag gctgccccccg atccaaaacca ccaaccgcat ccccaccacc    4800
cccgggaaag aaaccccccag caattggaag gcccctcccc ctcttcctca acacaagaac    4860
tccacaaccg aaccgcacaa gcgaccgagg tgacccaacc gcaggcatcc gactccctag    4920
acagatcctc tctccccggc aaactaaaca aaacttaggg ccaaggaaca tacacaccca    4980
acagaaccca gaccccggcc cacggcgccg cgccccaac cccgacaac cagagggagc    5040 ccccaaccaa tcccgccggc tccccccggtg cccacaggga gggacaccaa cccccgaaca    5100
gacccagcac ccaaccatcg acaatccaag acggggggc cccccaaaa aaaggccccc    5160 aggggccgac agccagcacc gcgaggaagc ccacccaccc cacacacgac cacggcaacc    5220
aaaccagaac ccagaccacc ctgggccacc agctcccaga ctcggccatc acccgcaga    5280 aaggaaaggc cacaacccgc gcaccccagc cccgatccgg cggggagcca cccaacccga    5340
accagcaccc aagagcgatc cccgaaggac ccccgaaccg caaggacat cagtatccca    5400 cagcctctcc aagtccccccg gtctcctcct cttctcgaag ggaccaaaag atcaatccac    5460
cacacccgac gacactcaac tccccacccc taaggagac accgggaatc ccagaatcaa    5520
gactcatcca atgtccatca tgggtctcaa ggtgaacgtc tctgccatat tcatggcagt    5580
actgttaact ctccaaacac ccaccggtca aatccattgg ggcaatctct ctaagatagg    5640
ggtggtagga ataggaagtg caagctacaa agttatgact cgttccagcc atcaatcatt    5700
agtcataaaa ttaatgccca atataactct cctcaataac tgcacgaggg tagagattgc    5760
agaatacagg agactactga gaacagtttt ggaaccaatt agagatgcac ttaatgcaat    5820
gacccagaat ataagaccgg ttcagagtgt agcttcaagt aggagacaca agagatttgc    5880
gggagtagtc ctggcaggtg cggccctagg cgttgccaca gctgctcaga taacagccgg    5940
```

```
cattgcactt caccagtcca tgctgaactc tcaagccatc gacaatctga gagcgagcct    6000
ggaaactact aatcaggcaa ttgagacaat cagacaagca gggcaggaga tgatattggc    6060
tgttcagggt gtccaagact acatcaataa tgagctgata ccgtctatga accaactatc    6120
ttgtgattta atcggccaga agctcgggct caaattgctc agatactata cagaaatcct    6180
gtcattattt ggccccagtt tacgggaccc catatctgcg gagatatcta tccaggcttt    6240
gagctatgcg cttggaggag acatcaataa ggtgttagaa aagctcggat acagtggagg    6300
tgatttactg ggcatcttag agagcggagg aataaaggcc cggataactc acgtcgacac    6360
agagtcctac ttcattgtcc tcagtatagc ctatccgacg ctgtccgaga ttaaggggt    6420 gattgtccac cggctagagg gggtctcgta caacataggc tctcaagagt ggtataccac    6480
tgtgcccaag tatgttgcaa cccaagggta ccttatctcg aattttgatg agtcatcgtg    6540
tactttcatg ccagagggga ctgtgtgcag ccaaaatgcc ttgtacccga tgagtcctct    6600
gctccaagaa tgcctccggg ggtacaccaa gtcctgtgct cgtacactcg tatccgggtc    6660
ttttgggaac cggttcattt tatcacaagg gaacctaata gccaattgtg catcaatcct    6720
ttgcaagtgt tacacaacag gaacgatcat taatcaagac cctgacaaga tcctaacata    6780
cattgctgcc gatcactgcc cggtagtcga ggtgaacggc gtgaccatcc aagtcgggag    6840
caggaggtat ccagacgctg tgtacttgca cagaattgac ctcggtcctc ccatatcatt    6900
ggagaggttg gacgtaggga caaatctggg gaatgcaatt gctaagttgg aggatgccaa    6960
ggaattgttg gagtcatcgg accagatatt gaggagtatg aaaggtttat cgagcactag    7020
catagtctac atcctgattg cagtgtgtct tggagggttg atagggatcc ccgctttaat    7080
atgttgctgc agggggcgtt gtaacaaaaa gggagaacaa gttggtatgt caagaccagg    7140
cctaaagcct gatcttacgg gaacatcaaa atcctatgta aggtcgctct gatcctctac    7200
aactcttgaa acacaaatgt cccacaagtc tcctcttcgt catcaagcaa ccaccgcacc    7260
cagcatcaag cccacctgaa attatctccg gcttccctct ggccgaacaa tatcggtagt    7320
taatcaaaac ttagggtgca agatcatcca caatgtcacc acaacgagac cggataaatg    7380
ccttctacaa agataacccc catcccaagg gaagtaggat agtcattaac agagaacatc    7440
ttatgattga tagaccttat gttttgctgg ctgttctgtt tgtcatgttt ctgagcttga    7500
tcgggttgct agccattgca ggcattagac ttcatcgggc agccatctac accgcagaga    7560
tccataaaag cctcagcacc aatctagatg taactaactc aatcgagcat caggtcaagg    7620
acgtgctgac accactcttc aaaatcatcg gtgatgaagt gggcctgagg acacctcaga    7680
gattcactga cctagtgaaa ttaatctctg acaagattaa attccttaat ccggataggg    7740
agtacgactt cagagatctc acttggtgta tcaacccgcc agagagaatc aaattggatt    7800
atgatcaata ctgtgcagat gtggctgctg aagagctcat gaatgcattg gtgaactcaa    7860
ctctactgga gaccagaaca accaatcagt tcctagctgt ctcaaaggga aactgctcag    7920
ggcccactac aatcagaggt caattctcaa acatgtcgct gtccctgtta gacttgtatt    7980
taggtcgagg ttacaatgtg tcatctatag tcactatgac atcccaggga atgtatgggg    8040
gaacttacct agtggaaaag cctaatctga gcagcaaaag gtcagagttg tcacaactga    8100
gcatgtaccg agtgtttgaa gtaggtgtta tcagaaatcc gggttttggg gctccggtgt    8160
tccatatgac aaactatctt gagcaaccag tcagtaatga tctcagcaac tgtatggtgg    8220 cttttggggga gctcaaactc gcagcccttt gtcacgggga agattctatc acaattccct    8280
atcagggatc agggaaaggt gtcagcttcc agctcgtcaa gctaggtgtc tggaaatccc    8340
```

```
caaccgacat gcaatcctgg gtccccttat caacggatga tccagtgata gacaggcttt    8400
acctctcatc tcacagaggt gttatcgctg acaatcaagc aaaatgggct gtcccgacaa    8460
cacgaacaga tgacaagttg cgaatggaga catgcttcca acaggcgtgt aagggtaaaa    8520
tccaagcact ctgcgagaat cccgagtggg caccattgaa ggataacagg attccttcat    8580
acggggtctt gtctgttgat ctgagtctga cagttgagct taaaatcaaa attgcttcgg    8640
gattcgggcc attgatcaca cacggttcag ggatggacct atacaaatcc aaccacaaca    8700
atgtgtattg gctgactatc ccgccaatga agaacctagc cttaggtgta atcaacacat    8760
tggagtggat accgagattc aaggttagtc cctacctctt cactgtccca attaaggaag    8820
caggcgaaga ctgccatgcc ccaacatacc tacctgcgga ggtggatggt gatgtcaaac    8880
tcagttccaa tctggtgatt ctacctggtc aagatctcca atatgttttg gcaacctacg    8940
atacttccag ggttgaacat gctgtggttt attacgttta cagcccaagc cgctcatttt    9000
cttactttta tccttttagg ttgcctataa aggggtccc catcgaatta caagtggaat    9060
gcttcacatg ggaccaaaaa ctctggtgcc gtcacttctg tgtgcttgcg gactcagaat    9120
ctggtggaca tatcactcac tctgggatgg tgggcatggg agtcagctgc acagtcaccc    9180
gggaagatgg aaccaatcgc agatagggct gctagtgaac caatcacatg atgtcaccca    9240
gacatcaggc atacccacta gtgtgaaata gacatcagaa ttaagaaaaa cgtagggtcc    9300
aagtggttcc ccgttatgga ctcgctatct gtcaaccaga tcttataccc tgaagttcac    9360
ctagatagcc cgatagttac caataagata gtagccatcc tggagtatgc tcgagtccct    9420
cacgcttaca gcctggagga ccctacactg tgtcagaaca tcaagcaccg cctaaaaaac    9480 ggatttttcca accaaatgat tataaacaat gtggaagttg gaatgtcat caagtccaag    9540 cttaggagtt atccggccca ctctcatatt ccatatccaa attgtaatca ggatttattt    9600
aacatagaag acaaagagtc aacgaggaag atccgtgaac tcctcaaaaa ggggaattcg    9660
ctgtactcca aagtcagtga taaggttttc caatgcttaa gggacactaa ctcacggctt    9720
ggcctaggct ccgaattgag ggaggacatc aaggagaaag ttattaactt gggagtttac    9780
atgcacagct cccagtggtt tgagcccttt ctgttttggt ttacagtcaa gactgagatg    9840
aggtcagtga ttaaatcaca aacccatact tgccatagga ggagacacac acctgtattc    9900
ttcactggta gttcagttga gttgctaatc tctcgtgacc ttgttgctat aatcagtaaa    9960
gagtctcaac atgtatatta cctgacattt gaactggttt tgatgtattg tgatgtcata    10020
gaggggaggt taatgacaga gaccgctatg actattgatg ctaggtatac agagcttcta    10080
ggaagagtca gatacatgtg gaaactgata gatggtttct tccctgcact cgggaatcca    10140
acttatcaaa ttgtagccat gctggagcct ctttcacttg cttacctgca gctgagggat    10200
ataacagtag aactcagagg tgctttcctt aaccactgct ttactgaaat acatgatgtt    10260
cttgaccaaa acgggttttc tgatgaaggt acttatcatg agttaactga agctctagat    10320 tacatttttca taactgatga catacatctg acaggggaga ttttctcatt tttcagaagt    10380
ttcggccacc ccagacttga agcagtaacg gctgctgaaa atgttaggaa atacatgaat    10440
cagcctaaag tcattgtgta tgagactctg atgaaaggtc atgccatatt ttgtggaatc    10500
ataatcaacg gctatcgtga caggcacgga ggcagttggc caccgctgac cctccccctg    10560
catgctgcag acacaatccg gaatgctcaa gcttcaggtg aagggttaac acatgagcag    10620
tgcgttgata actggaaatc ttttgctgga gtgaaatttg gctgctttat gcctcttagc    10680
```

```
ctggatagtg atctgacaat gtacctaaag gacaaggcac ttgctgctct ccaaagggaa    10740
tgggattcag tttacccgaa agagttcctg cgttacgacc ctcccaaggg aaccgggtca    10800
cggaggcttg tagatgtttt ccttaatgat tcgagctttg acccatatga tgtgataatg    10860
tatgttgtaa gtggagctta cctccatgac cctgagttca acctgtctta cagcctgaaa    10920
gaaaaggaga tcaaggaaac aggtagactt tttgctaaaa tgacttacaa aatgagggca    10980
tgccaagtga ttgctgaaaa tctaatctca aacgggattg gcaaatattt taaggacaat    11040
gggatggcca aggatgagca cgatttgact aaggcactcc acactctagc tgtctcagga    11100
gtccccaaag atctcaaaga aagtcacagg gggggccag tcttaaaaac ctactcccga    11160
agcccagtcc acacaagtac caggaacgtg agagcagcaa aagggtttat agggttccct    11220
caagtaattc ggcaggacca agacactgat catccggaga atatggaagc ttacgagaca    11280
gtcagtgcat ttatcacgac tgatctcaag aagtactgcc ttaattggag atatgagacc    11340
atcagcttgt ttgcacagag gctaaatgag atttacggat tgccctcatt tttccagtgg    11400
ctgcataaga ggcttgagac ctctgtcctg tatgtaagtg accctcattg ccccccgac    11460 cttgacgccc atatcccgtt atataaagtc cccaatgatc aaatcttcat taagtaccct    11520
atgggaggta tagaagggta ttgtcagaag ctgtggacca tcagcaccat tccctatcta    11580
tacctggctg cttatgagag cggagtaagg attgcttcgt tagtgcaagg ggacaatcag    11640
accatagccg taacaaaaag ggtacccagc acatggccct acaaccttaa gaaacgggaa    11700
gctgctagag taactagaga ttactttgta attcttaggc aaaggctaca tgatattggc    11760
catcacctca aggcaaatga gacaattgtt tcatcacatt ttttgtcta ttcaaaagga    11820 atatattatg atgggctact tgtgtcccaa tcactcaaga gcatcgcaag atgtgtattc    11880
tggtcagaga ctatagttga tgaaacaagg gcagcatgca gtaatattgc tacaacaatg    11940
gctaaaagca tcgagagagg ttatgaccgt taccttgcat attccctgaa cgtcctaaaa    12000
gtgatacagc aaattctgat ctctcttggc ttcacaatca attcaaccat gacccgggat    12060
gtagtcatac ccctcctcac aaacaacgac ctcttaataa ggatggcact gttgcccgct    12120
cctattgggg ggatgaatta tctgaatatg agcaggctgt ttgtcagaaa catcggtgat    12180
ccagtaacat catcaattgc tgatctcaag agaatgattc tcgcctcact aatgcctgaa    12240
gagaccctcc atcaagtaat gacacaacaa ccggggggact ctcattcct agactgggct    12300 agcgacccct tactcagcaaa tcttgtatgt gtccagagca tcactagact cctcaagaac    12360
ataactgcaa ggtttgtcct gatccatagt ccaaacccaa tgttaaaagg attattccat    12420
gatgacagta agaagaggaa cgagggactg gcggcattcc tcatggacag gcatattata    12480
gtacctaggg cagctcatga aatcctggat catagtgtca caggggcaag agagtctatt    12540
gcaggcatgc tggataccac aaaaggcttg attcgagcca gcatgaggaa gggggggtta    12600
acctctcgag tgataaccag attgtccaat tatgactatg aacaattcag agcagggatg    12660
gtgctattga caggaagaaa gagaaatgtc ctcattgaca aagagtcatg ttcagtgcag    12720
ctggcgagag ctctaagaag ccatatgtgg gcgaggctag ctcgaggacg gcctatttac    12780
ggccttgagg tccctgatgt actagaatct atgcgaggcc accttattcg gcgtcatgag    12840
acatgtgtca tctgcgagtg tggatcagtc aactacggat ggttttttgt cccctcgggt    12900
tgccaactgg atgatattga caaggaaaca tcatccttga gagtcccata tattggttct    12960
accactgatg agagaacaga catgaagctt gccttcgtaa gagccccaag tcgatccttg    13020
cgatctgctg ttagaatagc aacagtgtac tcatgggctt acggtgatga tgatagctct    13080
```

```
tggaacgaag cctggttgtt ggctaggcaa agggccaatg tgagcctgga ggagctaagg      13140
gtgatcactc ccatctcaac ttcgactaat ttagcgcata ggttgaggga tcgtagcact      13200
caagtgaaat actcaggtac atcccttgtc cgagtggcga ggtataccac aatctccaac      13260
gacaatctct catttgtcat atcagataag aaggttgata ctaactttat ataccaacaa      13320
ggaatgcttc tagggttggg tgttttagaa acattgtttc gactcgagaa agataccgga      13380
tcatctaaca cggtattaca tcttcacgtc gaaacagatt gttgcgtgat cccgatgata      13440
gatcatccca ggatacccag ctcccgcaag ctagagctga gggcagagct atgtaccaac      13500
ccattgatat atgataatgc acctttaatt gacagagatg caacaaggct atacacccag      13560
agccatagga ggcaccttgt ggaatttgtt acatggtcca caccccaact atatcacatt      13620
ttagctaagt ccacagcact atctatgatt gacctggtaa caaaatttga aaggaccat      13680 atgaatgaaa tttcagctct catagggga tgacgatatca atagtttcat aactgagttt       13740
ctgctcatag agccaagatt attcactatc tacttgggcc agtgtgcggc catcaattgg      13800
gcatttgatg tacattatca tagaccatca gggaaatatc agatgggtga gctgttgtca      13860
tcgttccttt ctagaatgag caaaggagtg tttaaggtgc ttgtcaatgc tctaagccac      13920
ccaaagatct acaagaaatt ctggcattgt ggtattatag agcctatcca tggtccttca      13980
cttgatgctc aaaacttgca cacaactgtg tgcaacatgg tttacacatg ctatatgacc      14040
tacctcgacc tgttgttgaa tgaagagtta aagagttca catttctctt gtgtgaaagc      14100
gacgaggatg tagtaccgga cagattcgac aacatccagg caaaacactt atgtgttctg      14160
gcagatttgt actgtcaacc agggacctgc ccaccaattc gaggtctaag accggtagag      14220
aaatgtgcag ttctaaccga ccatatcaag gcagaggcta tgttatctcc agcaggatct      14280
tcgtggaaca taaatccaat tattgtagac cattactcat gctctctgac ttatctccgg      14340
cgaggatcga tcaaacagat aagattgaga gttgatccag gattcatttt cgacgccctc      14400
gctgaggtaa atgtcagtca gccaaagatc ggcagcaaca acatctcaaa tatgagcatc      14460
aaggctttca gacccccaca cgatgatgtt gcaaaattgc tcaaagatat caacacaagc      14520
aagcacaatc ttcccatttc aggggcaat ctcgccaatt atgaaatcca tgcttccgc       14580 agaatcgggt tgaactcatc tgcttgctac aaagctgttg agatatcaac attaattagg      14640
agatgccttg agccagggga ggacggcttg ttcttgggtg agggatcggg ttctatgttg      14700
atcacttata aagagatact taaactaaac aagtgcttct ataatagtgg ggtttccgcc      14760
aattctagat ctggtcaaag ggaattagca ccctatccct ccgaagttgg ccttgtcgaa      14820
cacagaatgg gagtaggtaa tattgtcaaa gtgctcttta cgggaggcc cgaagtcacg      14880 tgggtaggca gtgtagattg cttcaatttc atagttagta atatccctac ctctagtgtg      14940
gggtttatcc attcagatat agagaccttg cctgacaaag atactataga gaagctagag      15000
gaattggcag ccatcttatc gatggctctg ctcctgggca aaataggatc aatactggtg      15060
attaagctta tgcctttcag cggggatttt gttcagggat ttataagtta tgtagggtct      15120
cattatagag aagtgaacct tgtataccct agatacagca acttcatctc tactgaatct      15180
tatttggtta tgacagatct caaggctaac cggctaatga atcctgaaaa gattaagcag      15240
cagataattg aatcatctgt gaggacttca cctggactta taggtcacat cctatccatt      15300
aagcaactaa gctgcataca agcaattgtg ggagacgcag ttagtagagg tgatatcaat      15360
cctactctga aaaaacttac acctatagag caggtgctga tcaattgcgg gttggcaatt      15420
```

```
aacggaccta agctgtgcaa agaattgatc caccatgatg ttgcctcagg gcaagatgga    15480
ttgcttaatt ctatactcat cctctacagg gagttggcaa gattcaaaga caaccaaaga    15540
agtcaacaag ggatgttcca cgcttacccc gtattggtaa gtagcaggca acgagaactt    15600
atatctagga tcacccgcaa attctggggg cacattcttc tttactccgg gaacaaaaag    15660
ttgataaata agtttatcca gaatctcaag tccggctatc tgatactaga cttacaccag    15720
aatatcttcg ttaagaatct atccaagtca gagaaacaga ttattatgac gggggggtttg   15780
aaacgtgagt gggtttttaa ggtaacagtc aaggagacca agaatggta taagttagtc     15840
ggatacagtg ccctgattaa ggactaattg gttgaactcc ggaaccctaa tcctgccta     15900
ggtggttagg cattatttgc aatatattaa agaaaacttt gaaaatacga gtttctatt     15960
cccagctttg tctggtggcc ggcatggtcc cagcctcctc gctggcgccg gctgggcaac    16020
attccgaggg gaccgtcccc tcggtaatgg cgaatgggac gcggccgatc cggctgctaa    16080
caaagcccga aggaagctg agttggctgc tgccaccgct gagcaataac tagcataacc      16140
ccttggggcc tctaaacggg tcttgagggg ttttttgctg aaaggaggaa ctatatccgg    16200
atgcggccgc gggccctatg gtacccagct tttgttccct ttagtgaggg ttaattccga    16260
gcttggcgta atcatggtca tagctgtttc ctgtgtgaaa ttgttatccg ctcacaattc    16320
cacacaacat aggagccgga agcataaagt gtaaagcctg gggtgcctaa tgagtgaggt    16380
aactcacatt aattgcgttg cgctcactgc ccgctttcca gtcgggaaac ctgtcgtgcc    16440
agctgcatta atgaatcggc caacgcgcgg ggagaggcgg tttgcgtatt gggcgctctt    16500
ccgcttcctc gctcactgac tcgctgcgct cggtcgttcg gctgcggcga gcggtatcag    16560
ctcactcaaa ggcggtaata cggttatcca cagaatcagg gataacgca ggaaagaaca     16620
tgtgagcaaa aggccagcaa aaggccagga accgtaaaaa ggccgcgttg ctggcgtttt    16680
tccataggct cggccccct gacgagcatc acaaaaatcg acgctcaagt cagaggtggc     16740
gaaacccgac aggactataa agataccagg cgttccccc tggaagctcc ctcgtgcgct     16800
ctcctgttcc gaccctgccg cttaccggat acctgtccgc ctttctccct cgggaagcg    16860
tggcgctttc tcaatgctca cgctgtaggt atctcagttc ggtgtaggtc gttcgctcca    16920
agctgggctg tgtgcacgaa ccccccgttc agcccgaccg ctgcgcctta ccggtaact     16980
atcgtcttga gtccaacccg gtaagacacg acttatcgcc actggcagca gccactggta   17040
acaggattag cagagcgagg tatgtaggcg gtgctacaga gttcttgaag tggtggccta    17100
actacggcta cactagaagg acagtatttg gtatctgcgc tctgctgaag ccagttacct    17160
tcggaaaaag agttggtagc tcttgatccg gcaaacaaac caccgctggt agcggtggtt    17220
tttttgtttg caagcagcag attacgcgca gaaaaaagg atctcaagaa gatcctttga     17280
tcttttctac ggggtctgac gctcagtgga acgaaaactc acgttaaggg attttggtca    17340
tgagattatc aaaaaggatc ttcacctaga tccttttaaa ttaaaaatga agttttaaat    17400
caatctaaag tatatatgag taaacttggt ctgacagtta ccaatgctta atcagtgagg    17460
cacctatctc agcgatctgt ctatttcgtt catccatagt tgcctgactg cccgtcgtgt    17520
agataactac gatacgggag ggcttaccat ctggccccag tgctgcaatg ataccgcgag    17580
acccacgctc accggctcca gatttatcag caataaacca gccagccgga agggccgagc    17640
gcagaagtgg tcctgcaact ttatccgcct ccatccagtc tattaattgt tgccgggaag    17700
ctagagtaag tagttcgcca gttaatagtt tgcgcaacgt tgttgccatt gctacaggca    17760
tcgtggtgtc acgctcgtcg tttggtatgg cttcattcag ctccggttcc caacgatcaa    17820
```

-continued

```
ggcgagttac atgatccccc atgttgtgaa aaaaagcggt tagctccttc ggtcctccga    17880
tcgttgtcag aagtaagttg gccgcagtgt tatcactcat gcttatggca gcactgcata    17940
attctcttac tgtcatgcca tccgtaagat gcttttctgt gactggtgag tactcaacca    18000
agtcattctg agaatagtgt atgcggcgac cgagttgctc ttgcccggcg tcaatacggg    18060
ataataccgc gccacatagc agaactttaa aagtgctcat cattggaaaa cgttcttcgg    18120
ggcgaaaact ctcaaggatc ttaccgctgt tgagatccag ttcgatgtaa cccactcgtg    18180
cacccaactg atcttcagca tcttttactt tcaccagcgt ttctgggtga gcaaaaacag    18240
gaaggcaaaa tgccgcaaaa aagggaataa gggcgacacg gaaatgttga atactcatac    18300
tcttcctttt tcaatattat tgaagcattt atcagggtta ttgtctcatg agcggataca    18360
tatttgaatg tatttagaaa aataaacaaa taggggttcc gcgcacattt ccccgaaaag    18420
tgccacctga aattgtaaac gttaatattt tgttaaaatt cgcgttaaat ttttgttaaa    18480
tcagctcatt ttttaaccaa taggccgaaa tcggcaaaat cccttataaa tcaaaagaat    18540
agaccgagat agggttgagt gttgttccag tttggaacaa gagtccacta ttaaagaacg    18600
tggactccaa cgtcaaaggg cgaaaaaccg tctatcaggg cgatggccca ctacgtgaac    18660
catcacccta atcaagtttt tggggtcga ggtgccgtaa agcactaaat cggaaccta     18720 aagggagccc ccgatttaga gcttgacggg gaaagccggc gaacgtggcg agaaaggaag    18780
ggaagaaagc gaaaggagcg ggcgctaggg cgctggcaag tgtagcggtc acgctgcgcg    18840
taaccaccac acccgccgcg cttaatgcgc cgctacaggg cgcgtcccat tcgccattca    18900
ggctgcgcaa ctgttgggaa gggcgatcgg tgcgggcctc ttcgctatta cgccagccac    18960
cgcggtg                                                              18967
```

<210> SEQ ID NO 83
<211> LENGTH: 843
<212> TYPE: DNA
<213> ORGANISM: Artificial Sequence
<220> FEATURE:
<223> OTHER INFORMATION: Description of Artificial Sequence: Synthetic
      ATU sequence
<220> FEATURE:
<221> NAME/KEY: misc_feature
<222> LOCATION: (1)..(85)
<223> OTHER INFORMATION: additional sequence (copy of the N-P intergenic
      region of measles virus) plus cloning sites
<220> FEATURE:
<221> NAME/KEY: misc_feature
<222> LOCATION: (86)..(805)
<223> OTHER INFORMATION: inserted enhanced GFP sequence
<220> FEATURE:
<221> NAME/KEY: misc_feature
<222> LOCATION: (806)..(843)
<223> OTHER INFORMATION: additional sequence (copy of the N-P intergenic
      region of measles virus) plus cloning site
<220> FEATURE:
<221> NAME/KEY: misc_feature
<222> LOCATION: (834)..(834)
<223> OTHER INFORMATION: substituted C represents the mutation which
      distinguishes normal ATU from bis (in pTM-MVSchw2-gfp and
      pTM-MVSchw2-GFPbis)

<400> SEQUENCE: 83

```
actagcctac cctccatcat tgttataaaa aacttaggaa ccaggtccac acagccgcca      60
gcccatcaac gcgtacgtag cgcgcatggt gagcaagggc gaggagctgt tcaccggggt     120
ggtgcccatc ctggtcgagc tggacggcga cgtaaacggc cacaagttca gcgtgtccgg     180
cgagggcgag ggcgatgcca cctacggcaa gctgaccctg aagttcatct gcaccaccgg     240
```

```
caagctgccc gtgccctggc ccaccctcgt gaccaccctg acctacggcg tgcagtgctt    300
cagccgctac cccgaccaca tgaagcagca cgacttcttc aagtccgcca tgcccgaagg    360
ctacgtccag gagcgcacca tcttcttcaa ggacgacggc aactacaaga cccgcgccga    420
ggtgaagttc gagggcgaca ccctggtgaa ccgcatcgag ctgaagggca tcgacttcaa    480
ggaggacggc aacatcctgg ggcacaagct ggagtacaac tacaacagcc acaacgtcta    540
tatcatggcc gacaagcaga gaacggcat caaggtgaac ttcaagatcc gccacaacat     600
cgaggacggc agcgtgcagc tcgccgacca ctaccagcag aacacccca tcggcgacgg     660
ccccgtgctg ctgcccgaca accactacct gagcacccag tccgccctga gcaaagaccc    720
caacgagaag cgcgatcaca tggtcctgct ggagttcgtg accgccgccg ggatcactct    780
cggcatggac gagctgtaca agtagtgagc gcgcagcgct gacgtctcgc gatcgatgct    840
agc                                                                  843
```

<210> SEQ ID NO 84
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Ser His Met Ser Arg His His Ile Pro Ser Gly Ala Arg Ser Thr
1               5                   10                  15

Phe Phe Ile Asp Gln Ser Arg
            20

<210> SEQ ID NO 85
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Glu Thr Tyr Thr Leu Cys Tyr Tyr Thr Ser Ser Arg Ala Gly Tyr Ile
1               5                   10                  15

Phe Thr Ile Glu Arg Asn Arg
            20

<210> SEQ ID NO 86
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Thr Tyr Thr Leu Cys Tyr Tyr Thr Ser Phe Arg Thr Gly Tyr Thr
1               5                   10                  15

Leu Thr Thr Glu Arg Asn Lys
            20

<210> SEQ ID NO 87
<211> LENGTH: 54
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 87
caatacagtc ctgcccctta ccgagtcttg cacactcttt cattgtaacg gatg            54

<210> SEQ ID NO 88
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gagagccatt tcgtttttca tcgaactcag tgtgactcct cctaagcgtg accg            54

<210> SEQ ID NO 89
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ggaagacatt tcgttttgca ttgaatttaa tgtgacccccc accaagagta acca           54

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ttataaaaaa cttaggaacc aggtcca                                          27

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ttataaaaaa cttaggagca aagt                                             24
```

INFECTIOUS CDNA OF AN APPROVED VACCINE STRAIN OF MEASLES VIRUS, USE FOR IMMUNOGENIC COMPOSITIONS

SEQUENCE LISTING

The instant application contains a Sequence Listing which has been submitted electronically in ASCII format and is hereby incorporated by reference in its entirety. Said ASCII copy, created on Jun. 13, 2016, is named DI2001_40C_SL.txt and is 48,666 bytes in size.

Measles virus is a member of the order mononegavirales, i.e., viruses with a non-segmented negative-strand RNA genome. The non segmented genome of measles virus (MV) has an antimessage polarity which results in a genomic RNA which is neither translated in vivo or in vitro nor infectious when purified. Transcription and replication of non-segmented (−) strand RNA viruses and their assembly as virus particles have been studied and reported especially in Fields virology (3$^{rd}$ edition, vol. 1, 1996, Lippincott—Raven publishers—Fields B N et al). Transcription and replication of measles virus do not involve the nucleus of the infected cells but rather take place in the cytoplasm of said infected cells. The genome of the measles virus comprises genes encoding six major structural proteins from the six genes (designated N, P, M, F, H and L) and an additional two-non structural proteins from the P. gene. The gene order is the following: 3', N, P (including C and V), M, F, H, and L large polymerase protein at the 5' end. The genome further comprises non coding regions in the intergenic region M/F; this non-coding region contains approximately 1000 nucleotides of untranslated RNA. The cited genes respectively encode the leader peptide (I gene), the proteins of the nucleocapsid of the virus, i.e., the nucleoprotein (N), the phosphoprotein (P), and the large protein (L) which assemble around the genome RNA to provide the nucleocapsid. The other genes encode the proteins of viral envelope including the hemagglutinin (H), the fusion (F) and the matrix (M) proteins.

The measles virus has been isolated and live attenuated vaccines have been derived from the Edmonston MV isolated in 1954 (Enders, J. F., and T. C. Peebles. 1954. Propagation in tissue cultures od cytopathogenic agents from patients with measles. Proc. Soc. Exp. Biol. Med. 86:277-286.), by serially passages performed on primary human kidney or amnion cells. The used strains were then adapted to chicken embryo fibroblasts (CEF) to produce Edmonston A and B seeds (Griffin, D., and W. Bellini. 1996. Measles virus, p. 1267-1312. In B. Fields, D. Knipe, et al. (ed.), Virology, vol. 2. Lippincott—Raven Publishers, Philadelphia). Edmonston B was licensed in 1963 as the first MV vaccine. Further passages of Edmonston A and B on CEF produced the more attenuated Schwarz and Moraten viruses (Griffin, D., and W. Bellini. 1996. Measles virus, p. 1267-1312. In B. Fields, D. Knipe, et al. (ed.), Virology, vol. 2. Lippincott—Raven Publishers, Philadelphia) whose sequences have recently been shown to be identical (Parks, C. L., R. A. Lerch, P. Walpita, H. P. Wang, M. S. Sidhu, and S. A. Udem. 2001. Analysis of the noncoding regions of measles virus strains in the Edmonston vaccine lineage. J Virol. 75:921-933; Parks, C. L., R. A. Lerch, P. Walpita, H. P. Wang, M. S. Sidhu, and S. A. Udem. 2001. Comparison of predicted amino acid sequences of measles virus strains in the Edmonston vaccine lineage. J Virol. 75:910-920). Because Edmonston B vaccine was reactogenic, it was abandoned in 1975 and replaced by the Schwarz/Moraten vaccine which is currently the most widely used measles vaccine in the world (Hilleman, M. 2002. Current overview of the pathogenesis and prophylaxis of measles with focus on practical implications. Vaccine. 20:651-665). Several other vaccine strains are also used: AIK-C, Schwarz F88, CAM70, TD97 in Japan, Leningrad-16 in Russia, and Edmonston Zagreb. The CAM70 and TD97 Chinese strains were not derived from Edmonston. Schwarz/Moraten and AIK-C vaccines are produced on CEF. Zagreg vaccine is produced on human diploid cells (WI-38).

The live attenuated vaccine derived from the Schwarz strain is commercialized by Aventis Pasteur (Lyon France) under the trademark Rouvax®.

In a noteworthy and pioneer work, Martin Billeter and colleagues cloned an infectious cDNA corresponding to the antigenome of Edmonston MV and established an original and efficient reverse genetics procedure to rescue the corresponding virus (Radecke, F., P. Spielhofer, H. Schneider, K. Kaelin, M. Huber, K. Dötsch, G. Christiansen, and M. Billeter., 1995. *Rescue of measles viruses from cloned DNA. EMBO Journal.* 14:5773-5784 and WO 97/06270 incorporated herewith by reference).

However, sequence comparison (see below) revealed that the genome cloned in this vector diverged from the Edmonston B sequence. It was closer to Edmonston-wt, an early passage on Vero cells of Edmonston isolate (Parks, C. L., R. A. Lerch, P. Walpita, H. P. Wang, M. S. Sidhu, and S. A. Udem. 2001. *Analysis of the noncoding regions of measles virus strains in the Edmonston vaccine lineage. J Virol.* 75:921-933; Parks, C. L., R. A. Lerch, P. Walpita, H. P. Wang, M. S. Sidhu, and S. A. Udem. 2001. *Comparison of predicted amino acid sequences of measles virus strains in the Edmonston vaccine lineage. J Virol.* 75:910-920), and had 10 amino acid substitutions not related to any Edmonston subgroup. Moreover, despite the fact that this vector is immunogenic in mice expressing CD46 and lacking the IFN type I receptor (19), the inventors show in the following experimental work that it is not immunogenic in non-human primates when inoculated at the standard dose of $10^4$ TCID$_{50}$. Therefore, this vector developed from a vaccine strain abandoned 25 years ago, and whose sequence diverged so much, does not appear suitable as vaccination vector, especially in human, while it certainly helps to understand some aspects of MV replication.

For these reasons, the inventors have decided that a measles vector aimed at children needs to be developed from an approved vaccine strain and have accordingly cloned an infectious cDNA starting from viral particles of the widely used Schwarz/Moraten strain of measles virus. This cDNA may allow the production of Schwarz/Moraten vaccine stocks without having to rely on the availability of seed stocks. It may also be used as a recombinant vaccination vector based on an approved and efficient vaccine strain, grown on CEF for safety reasons, and worldwide used. Such a vector may also be of interest for adult populations in certain circumstances where a need therefore exists.

DESCRIPTION OF THE INVENTION

The invention relates to a cDNA molecule which encodes the nucleotide sequence of the full length antigenomic (+)RNA strand of a measles virus (MV) originating from an approved vaccine strain.

The expression «encodes» in the above definition encompasses the capacity of the cDNA to allow transcription of a full length antigenomic (+)RNA, said cDNA serving especially as template for transcription. Accordingly, when the cDNA is a double stranded molecule, one of the strands has the same nucleotide sequence as the antigenomic (+) strand RNA of the measles virus, except that «U» nucleotides are substituted by «T» in the cDNA.

FIG. 5 illustrates the sequence of a DNA molecule of the invention which comprises a cDNA sequence as defined above, be it specified that the strand of the cDNA which is represented is identical to that of the antigenomic (+)RNA strand of a MV strain except for the substitution of «U» by «T».

The cDNA molecule according to the above definition allows the production, when placed in appropriate conditions, of an infectious antigenomic (+)RNA capable of producing infectious particles of the measles virus.

The cDNA obtained has especially the original 5'- and 3'-ends of the native antigenomic (+) strand of the viral RNA. In addition, the obtained cDNA complies with the rule of 6 which is required in order to express infectious viral particles.

The «rule of six» which is expressed in the fact that the total number of nucleotides present in the cDNA amounts to a multiple of six, rule which allows sufficient replication of genome RNA of the measles virus. It has been described in the above cited reference Fields Virology on page 1197.

The cDNA molecule of the invention which is derived from an MV approved vaccine strain can be obtained from the Schwarz or the Moraten strain.

These strains have been disclosed in several publications and used for the preparation of the currently used vaccines. The inventors propose especially the use of the Schwartz strain which is available from Aventis Pasteur (France).

According to another particular embodiment of the invention, the cDNA molecule is placed under the control of a heterologous expression control sequence.

The insertion of such a control for the expression of the cDNA, is favorable when the expression of this cDNA is sought in cell types which do not enable full transcription of the cDNA with its native control sequences.

According to a particular embodiment of the invention, the heterologous expression control sequence comprises the T7 promoter and T7 terminator sequences. These sequences are respectively located 5' and 3' of the coding sequence for the full length antigenomic (+)RNA strand of MV and from the adjacent sequences around this coding sequence.

In a particular embodiment of the invention, the cDNA molecule which is defined hereabove is modified i.e., comprises additional nucleotide sequences or motifs or comprises deletions or substitutions within said cDNA.

In a preferred embodiment, the cDNA molecule of the invention further comprises, at its 5'-end, adjacent to the first nucleotide of the nucleotide sequence encoding the full length antigenomic (+)RNA strand of the MV approved vaccine strain, a GGG motif followed by a hammerhead ribozyme sequence and which comprises, at its 3'-end, adjacent to the last nucleotide of said nucleotide sequence encoding the full length anti-genomic (+)RNA strand, the sequence of a ribozyme. The Hepatitis delta virus ribozyme (δ) is appropriate to carry out the invention.

The GGG motif placed at the 5' end, adjacent to the first nucleotide of the above coding sequence improves the efficiency of the transcription of said cDNA coding sequence. As a requirement for the proper assembly of measles virus particles is the fact that the cDNA encoding the antigenomic (+)RNA complies with the rule of six, when the GGG motif is added, a ribozyme is also added at the 5' end of the coding sequence of the cDNA, 3' from the GGG motif, in order to enable cleavage of the transcript at the first coding nucleotide of the full length antigenomic (+)RNA strand of MV.

Thus, in case where the GGG motif is added to improve efficiency of transcription, two ribozymes are added in order to ensure the cleavage of the coding sequence for the full length antigenomic (+)RNA strand of the MV.

According to the present invention, the expression "cDNA" encompasses a DNA molecule obtained by reverse transcription of an RNA molecule, including but not limited to an mRNA molecule.

Any other technique for the preparation of DNA, starting from the material disclosed in the present invention or using the disclosed features relating to the cDNA of the invention can be used, including techniques involving synthesis or PCR.

Therefore, the expression "cDNA" used for the description of the nucleotide sequence of the molecule of the invention merely relates to the fact that originally said molecule is obtained by reverse transcription of the full length genomic (−) RNA strand of the genome of viral particles of the measles virus. This should not be viewed as a limitation for the methods used for its preparation. Purified nucleic acids, including DNA are thus encompassed within the meaning cDNA according to the invention, provided said nucleic acid, especially DNA fulfils the above-given definitions.

The invention also concerns a cDNA molecule according to one of the above definitions which is comprised in a plasmid capable of replication.

Many plasmids can be prepared in order to fulfil the requirement of the invention and the invention especially relates to plasmid pTM-MVSchw which is represented on FIG. 2.

Plasmid pTM-MVSchw has been deposited at COLLECTION NATIONALE DE CULTURES DE MICROORGANISMES (CNCM), 25 rue du Docteur Roux, F-75724 Paris Cedex 15, France, on Jun. 12, 2002 under number I-2889. This plasmid is described in the examples and figures which follow. It is a plasmid vector derived from Bluescript, comprising the full length sequence coding for the measles virus, strain Schwarz, placed under the control of the promoter of the T7 RNA polymerase; its size is 18967 nucleotide.

The invention especially also relates to a cDNA molecule which is capable of producing infectious viral particles of the MV approved vaccine strain, preferably using the previously reported rescue system involving 293-3-46 helper cells (Radecke et al. and WO 97/06270), 293-3-46 helper cells expressing proteins necessary for transcription, replication of the RNA genome-sequence of MV from said cDNA and under conditions enabling viral particles assembly.

293-3-46 cells are cited as example for the preparation of the viral particles. They can however be replaced by any other appropriate cell line suitable for constituting helper cells.

Methods for the production of such infectious particles are given in the examples of the present application.

Particular preferred cDNA molecules according to the invention are the molecules having a nucleotide sequence selected among the following sequences:

the cDNA molecule which comprises the nucleotide sequence extending from nucleotide 83 to nucleotide 15977 of the sequence represented on FIG. 5, the cDNA molecule which comprises the nucleotide sequence extending from nucleotide 29 to nucleotide 16202 of the sequence represented on FIG. 5, the cDNA molecule which comprises the nucleotide sequence extending from nucleotide 26 to nucleotide 16202 of the sequence represented on FIG. 5, the cDNA molecule which comprises the nucleotide sequence extending from nucleotide 9 to nucleotide 16202 of the sequence represented on FIG. 5, the cDNA molecule which comprises the nucleotide sequence extending from nucleotide 29 to nucleotide 15977 of the sequence represented on FIG. 5, the cDNA molecule which comprises the nucleotide sequence extending from nucleotide 26 to nucleotide 15977 of the sequence represented on FIG. 5, the cDNA molecule which comprises the nucleotide sequence extending from nucleotide 9 to nucleotide 15977 of the sequence represented on FIG. 5.

The invention of course relates to each of the particular sequences described hereabove.

A particular cDNA molecule which is preferred to carry out the invention is the molecule which comprises the insert contained in plasmid pTMMVschw deposited at the CNCM under number I-2889, wherein said insert encodes a nucleotide sequence of the full length antigenomic (+)RNA strand of the measles virus. One particular insert is the one which is comprised within the sequence defined by the following restriction sites: NotI (located at position 1 on FIG. 5) and NotI (located at position 16203 on FIG. 5).

In a particular embodiment of the invention, the cDNA molecule is the product of the reverse transcription of the viral RNA purified from viral particles of the measles virus.

The preparation of the cDNA from viral purified RNA advantageously limits the presence of cellular components and especially cellular DNA or RNA which could be present in cells used for the cultivation of the virus. It limits especially the presence of viral genomic RNA which would be incomplete or mutated and which are present in cells, and limits the presence of viral mRNA present in large quantities in the cells.

The invention further relates to a cDNA molecule having the above defined features, which is capable of inducing an immune response against at least one antigen of a measles virus, when administered in vivo.

The invention also relates to a recombinant mononegavirales virus comprising the cDNA molecule of a measles virus according to anyone of the above definitions and a DNA sequence of a RNA virus, which recombinant virus is capable of eliciting in vivo a humoral and/or a cellular response against measles virus or against said RNA virus, or against both measles virus and RNA virus.

The invention also concerns a recombinant cDNA molecule as defined above, which further comprises a heterologous DNA sequence cloned therein in conditions enabling its expression as a heterologous amino acid sequence, said cloning being performed in such a way that the obtained recombinant cDNA complies with the rule of six.

Heterologous coding sequences especially DNA sequences are advantageously selected among sequences capable of expressing antigens or epitopes of antigens, having immunogenic properties and especially having the capacity of eliciting or favoring an immunogenic response in a host to which they are administered. Such heterologous DNA sequences can be derived for instance from antigens of pathogens.

The invention advantageously enables the insertion of such heterologous DNA sequences in a sequence which is designated an Additional Transcription Unit (ATU) especially an ATU as disclosed by Billeter et al. in WO 97/06270.

This ATU is especially represented on FIG. 4.

When used for the performance of the invention, the ATU is advantageously located in the N-terminal sequence of the cDNA molecule encoding the full-length (+)RNA strand of the antigenome of the MV and is especially located between the P and M genes of this virus or between the H and L genes. It has been observed that the transcription of the viral RNA of MV follows a gradient from the 5' to the 3' end. This explains that when inserted in the 5' end of the coding sequence of the cDNA, the ATU will enable a more efficient expression of the heterologous DNA sequence that it contains.

The invention also relates to a vector comprising a cDNA molecule as defined above including a recombinant cDNA. A particular vector is vector for cloning and/or expressing of this cDNA.

According to a preferred embodiment of the invention, the vector is a plasmid and is especially pTM-MVSchw deposited at the CNCM on Jun. 12, 2002 under No. I-2889.

Other vectors, designated pTM-MVSchw2-gfp deposited at the CNCM under no I-2890 on Jun. 12, 2002 or designated pTM-MVSchw2-GFPbis deposited at the CNCM under no I-3034 on May 26, 2003 are encompassed within the invention.

These vectors are derived from pTM-MVSchw, and are accordingly plasmid vectors derived from Bluescript, comprising the full length sequence coding for the measles virus, strain Schwarz, placed under the control of the promoter of the T7 RNA polymerase, and further containing the gfp gene coding for the GFP protein, said gene being inserted in an ATU at position 2 (i.e., between the N and P genes of MV).

The size of pTM-MvSchw is 18967 nucleotides. The size of pTM-MVSchw2-gfp is 19800 nucleotides.

The difference between pTM-MVSchw2-gfp and pTM-MVSchw2-GFPbis corresponds to a mutation in the ATU sequence where a C nucleotide is substituted as illustrated on FIG. 4B at the end of the ATU, to provide pTM-MVSchw2-GFPbis.

The invention also relates to a process for the preparation of infectious measles virus particles comprising: 1) expressing the cDNA of the invention according to one of the above definitions or the vector containing such cDNA in a helper cell line which also expresses proteins necessary for transcription, replication and encapsidation of the antigenomic (+)RNA sequence of MV from said cDNA and under conditions enabling viral particles assembly and recovering the expressed viral particles.

According to a particular embodiment of this process, it comprises: transfecting helper cells with a cDNA according to the above definition with a vector above defined, wherein said helper cells are capable of expressing helper functions to express an RNA polymerase, and to express the N, P and L proteins of the MV virus; co-cultivating said transfected helper cells of step 1) with passaged cells suitable for the passage of the MV vaccine strain from which the cDNA originates; recovering the infectious MV viral particles produced.

According to a preferred embodiment, helper cells are derived from human embryonic kidney cell line 293, which cell line 293 is deposited with the ATCC under No. CRL-1573.

According to another aspect of this process, the cells suitable for passage are CEF cells.

CEF cells can be prepared from fertilized chicken eggs as obtained from EARL Morizeau, 8 rue Moulin, 28190 Dangers, France, or from any other producer of fertilized chicken eggs.

The process which is disclosed according to the present invention is used advantageously for the production of infectious measles virus appropriate for use as vaccine compositions.

The invention thus relates to an immunogenic composition whose active principle comprises infection measles viral particles obtained by the process disclosed above.

The invention also concerns a vaccine composition. Such a vaccine composition has advantageously an active principle which comprises measles virus particles rescued from the cDNA of the vector which has been defined hereabove, which is expressed in a helper cell based rescue system.

Advantageously, such a vaccine composition is suitable for protection against measles virus. According to the embodiment where the cDNA is recombined with a heterologous DNA sequence encoding an immunogenic amino acid sequence, the vaccine composition can further be suitable for protection against the pathogen from which the immunogenic DNA sequence derives.

The invention also concerns a cell which is recombined with a cDNA molecule according to the invention or with a vector as defined above. A preferred cell is a prokaryotic cell such as *E. coli* or *Salmonella*.

Another preferred cell is a eukaryotic cell, especially a cell selected among yeasts, such as *Saccharomyces Cerevisiae*.

A cell within the definition of the invention, can be characterized according to a particular embodiment by the fact that this comprises nucleotide sequences expressing helper functions necessary to express an RNA polymerase and to express the N, P and L proteins of the MV virus. Such a cell can thus be used for the rescue of the viral particles.

The examples and figures which follow provide additional features for the characterization of the invention.

Figures 1A, 1B:
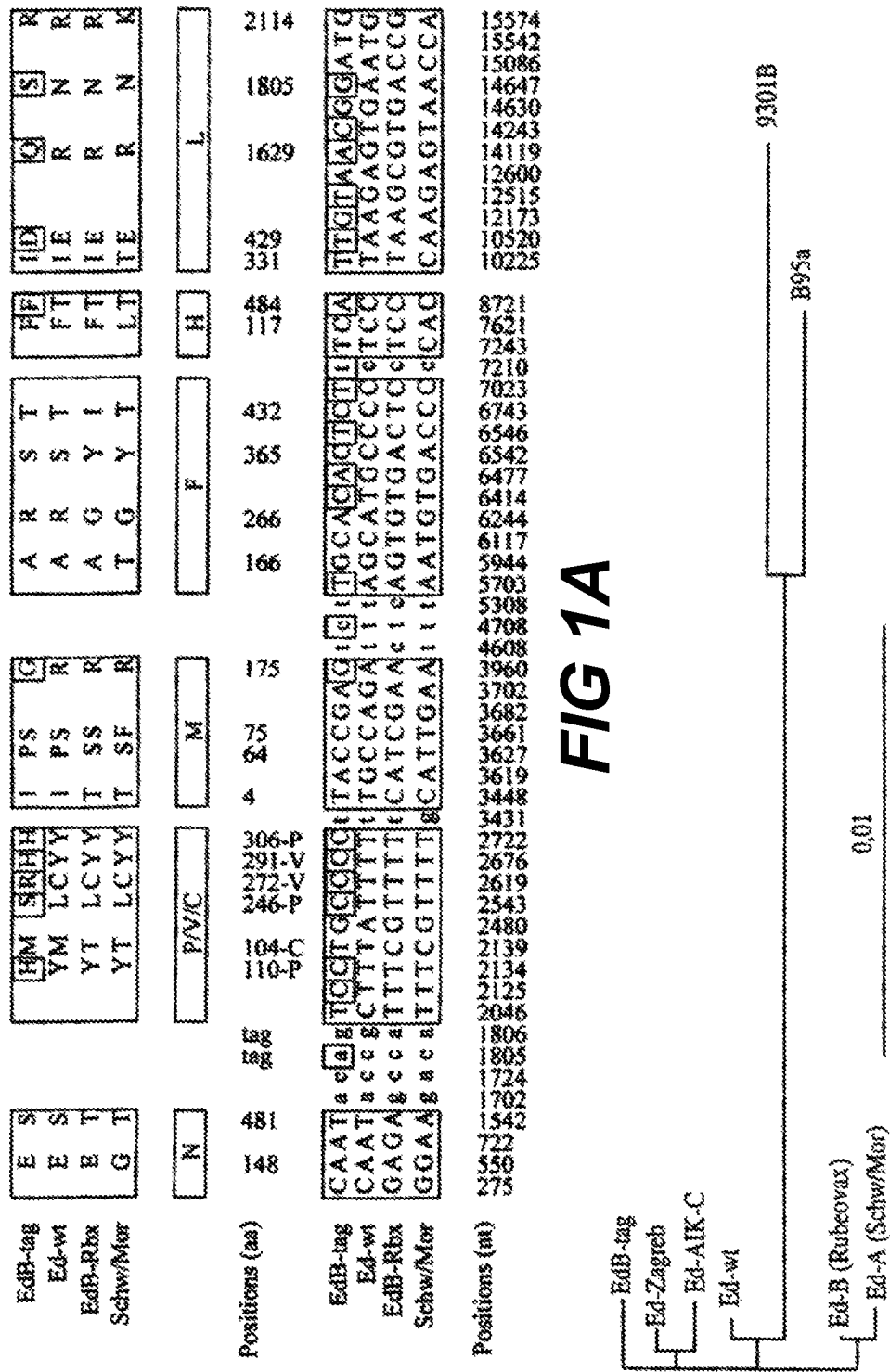
FIGS. 1A and 1B. Comparison of MV genomes. (A) Nucleotide changes for each coding region (capital letters in boxes) and in non-coding regions (lower case letters) are shown in the lower part (EdB-tag: SEQ ID NO: 87; EdB-Rbx: SEQ ID NO:88; Schw/Mor: SEQ ID NO: 89). Amino acid changes are shown in the upper part (one-letter amino acid symbol) (EdB-tag: SEQ ID NO: 84; EdB-Rbx: SEQ ID NO:85; Schw/Mor: SEQ ID NO: 86). Yellow color in the grid shows the wt substitutions. Blue color indicates the substitutions corresponding to the Rubeovax/Scwharz/moraten vaccine type. The red color shows the nucleotide and amino acid changes that are present only in the EdB-tag sequence. Nucleotide changes in positions 1805 and 1806 of EdB-tag correspond to the tag introduced. (B) Phylogenetic tree showing the EdB-tag among the Edmonston group and two wt isolates (Takeda, M., A. Kato, F. Kobune, H. Sakata, Y. Li, T. Shioda, Y. Sakai, M. Asakawa, and Y. Nagai. 1998. Measles virus attenuation associated with transcriptional impediment and a few amino acid changes in the polymerase and accessory proteins. J Virol. 72:8690-8696; Takeuchi, K., N. Miyajima, F. Kobune, and M. Tashiro. 2000. Comparative nucleotide sequence analyses of the entire genomes of B95a cell-isolated and vero cell-isolated measles viruses from the same patient. Virus Genes. 20:253-257). The sequences were aligned using Clustal W (Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-4680). Nucleotide sequence distance were determined with Dnadist of the Phylip package version 3.5 'Felsenstein, J. 1989. Cladistics. 5:164-166. The tree was derived by neighbor-joining analysis applied to pairwise sequence distances calculated using a variety of methods including the Kimura two-parameter method to generate unrooted trees. The final output was generated with Treeview (Page, R. D. 1996. TreeView: an application to display phylogenetic trees on personal computers. Comput Appl Biosci. 12:357-358).

| N° Sense | Position | N° Antisense |
|---|---|---|
| 1 ATCCGAGATGGCCACACTTT (SEQ ID NO: 1) | 101 | 1a AAAGTGTGGCCATCTCGGAT (SEQ ID NO: 2) |
| 2 TGATTCTGGGTACCATCCTA (SEQ ID NO: 3) | 601 | 2a TAGGATGGTACCCAGAATCA (SEQ ID NO: 4) |
| 3 TATGCCATGGGAGTAGGAGT (SEQ ID NO: 5) | 1110 | 3a ACTCCTACTCCCATGGCATA (SEQ ID NO: 6) |
| 4 TGGCAGGAATCTCGGAAGAA (SEQ ID NO: 7) | 1609 | 4a TTCTTCCGAGATTCCTGCCA (SEQ ID NO: 8) |
| 5 GCATCAAGCACTGGGTTACA (SEQ ID NO: 9) | 2110 | 5a TGTAACCCAGTGCTTGATGC (SEQ ID NO: 10) |
| 6 TACAGGAGTGGACACCCGAA (SEQ ID NO: 11) | 2651 | 6a TTCGGGTGTCCACTCCTGTA (SEQ ID NO: 12) |
| 7 AGGACAGCTGCTGAAGGAAT (SEQ ID NO: 13) | 3096 | 7a ATTCCTTCAGCAGCTGTCCT (SEQ ID NO: 14) |
| 8 TTGTTGAGGACAGCGATTCC (SEQ ID NO: 15) | 3610 | 8a GGAATCGCTGTCCTCAACAA (SEQ ID NO: 16) |

-continued

| N° Sense | Position | N° Antisense |
|---|---|---|
| 9 AGAGTGAAGTCTACTCTGCC (SEQ ID NO: 17) | 4120 | 9a GGCAGAGTAGACTTCACTCT (SEQ ID NO: 18) |
| 10 TGACACAAGGCCACCACCAG (SEQ ID NO: 19) | 4608 | 10a CTGGTGGTGGCCTTGTGTCA (SEQ ID NO: 20) |
| 11 AGCTCCCAGACTCGGCCATC (SEQ ID NO: 21) | 5169 | 11a GATGGCCGAGTCTGGGAGCT (SEQ ID NO: 22) |
| 12 CCAGCCATCAATCATTAGTC (SEQ ID NO: 23) | 5603 | 12a GACTAATGATTGATGGCTGG (SEQ ID NO: 24) |
| 13 AGTTTACGGGACCCCATATC (SEQ ID NO: 25) | 6115 | 13a GATATGGGGTCCCGTAAACT (SEQ ID NO: 26) |
| 14 GGAACCTAATAGCCAATTGT (SEQ ID NO: 27) | 6608 | 14a ACAATTGGCTATTAGGTTCC (SEQ ID NO: 28) |
| 15 CTCTTCGTCATCAAGCAACC (SEQ ID NO: 29) | 7151 | 15a GGTTGCTTGATGACGAAGAG (SEQ ID NO: 30) |
| 16 TCACTTGGTGTATCAACCCG (SEQ ID NO: 31) | 7677 | 16a CGGGTTGATACACCAAGTGA (SEQ ID NO: 32) |
| 17 AACTGTATGGTGGCTTTGGG (SEQ ID NO: 33) | 8126 | 17a CCCAAAGCCACCATACAGTT (SEQ ID NO: 34) |
| 18 TGTGTATTGGCTGACTATCC (SEQ ID NO: 35) | 8620 | 18a GGATAGTCAGCCAATACACA (SEQ ID NO: 36) |
| 19 ATCAGGCATACCCACTAGTG (SEQ ID NO: 37) | 9162 | 19a CACTAGTGGGTATGCCTGAT (SEQ ID NO: 38) |
| 20 GCACAGCTCCCAGTGGTTTG (SEQ ID NO: 39) | 9701 | 20a CAAACCACTGGGAGCTGTGC (SEQ ID NO: 40) |
| 21 TCATGAGTTAACTGAAGCTC (SEQ ID NO: 41) | 10214 | 21a GAGCTTCAGTTAACTCATGA (SEQ ID NO: 42) |
| 22 GTCACGGAGGCTTGTAGATG (SEQ ID NO: 43) | 10715 | 22a CATCTACAAGCCTCCGTGAC (SEQ ID NO: 44) |
| 23 GTACTGCCTTAATTGGAGAT (SEQ ID NO: 45) | 11231 | 23a ATCTCCAATTAAGGCAGTAC (SEQ ID NO: 46) |
| 24 TGATGGGCTACTTGTGTCCC (SEQ ID NO: 47) | 11747 | 24a GGGACACAAGTAGCCCATCA (SEQ ID NO: 48) |
| 25 ACCCTTACTCAGCAAATCTT (SEQ ID NO: 49) | 12223 | 25a AAGATTTGCTGAGTAAGGGT (SEQ ID NO: 50) |
| 26 TCTATGCGAGGCCACCTTAT (SEQ ID NO: 51) | 12726 | 26a ATAAGGTGGCCTCGCATAGA (SEQ ID NO: 52) |
| 27 TTGTCCGAGTGGCGAGGTAT (SEQ ID NO: 53) | 13144 | 27a ATACCTCGCCACTCGGACAA (SEQ ID NO: 54) |
| 28 CAATTGGGCATTTGATGTAC (SEQ ID NO: 55) | 13712 | 28a GTACATCAAATGCCCAATTG (SEQ ID NO: 56) |
| 29 GAGGCTATGTTATCTCCAGC (SEQ ID NO: 57) | 14172 | 29a GCTGGAGATAACATAGCCTC (SEQ ID NO: 58) |
| 30 AGTTGGCCTTGTCGAACACA (SEQ ID NO: 59) | 14723 | 30a TGTGTTCGACAAGGCCAACT (SEQ ID NO: 60) |
| 31 CTGGACTTATAGGTCACATC (SEQ ID NO: 61) | 15190 | 31a GATGTGACCTATAAGTCCAG (SEQ ID NO: 62) |
| 32 GGTTTGAAACGTGAGTGGGT (SEQ ID NO: 63) | 15693 | 32a ACCCACTCACGTTTCAAACC (SEQ ID NO: 64) |

Figure 3B:
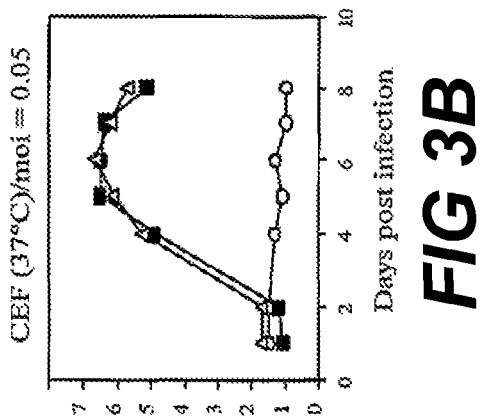
Figure 3C:
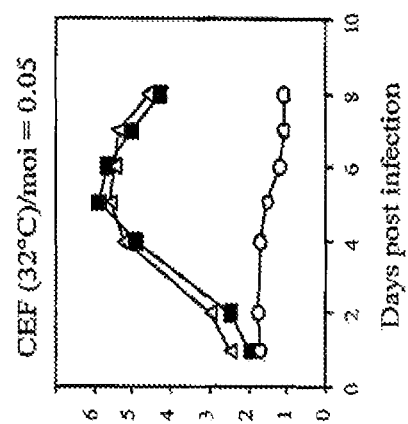
Figure 3A:
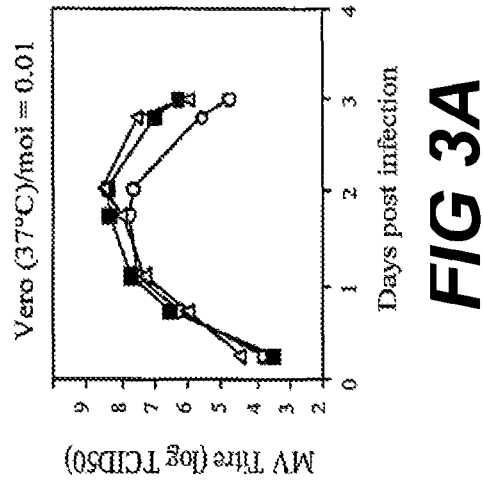

FIGS. 3A, 3B, and 3C. Growth kinetics of rescued Schwarz and EdB-tag viruses on Vero and CEF cells. Cells on 35 mm dishes were infected with Schwarz MV rescued from pTM-MVSchw plasmid (-■-), EdB-tag MV (-○-), and industrial Schwarz virus (-△-) at different MOI (as indicated). At each time point, cells were collected and cell-associated virus titers were determined using the $TCID_{50}$ method on Vero cells. (A) Vero cells incubated at 37° C., (B) CEF incubated at 37° C., (C) CEF incubated at 32° C.

Figure 4A:
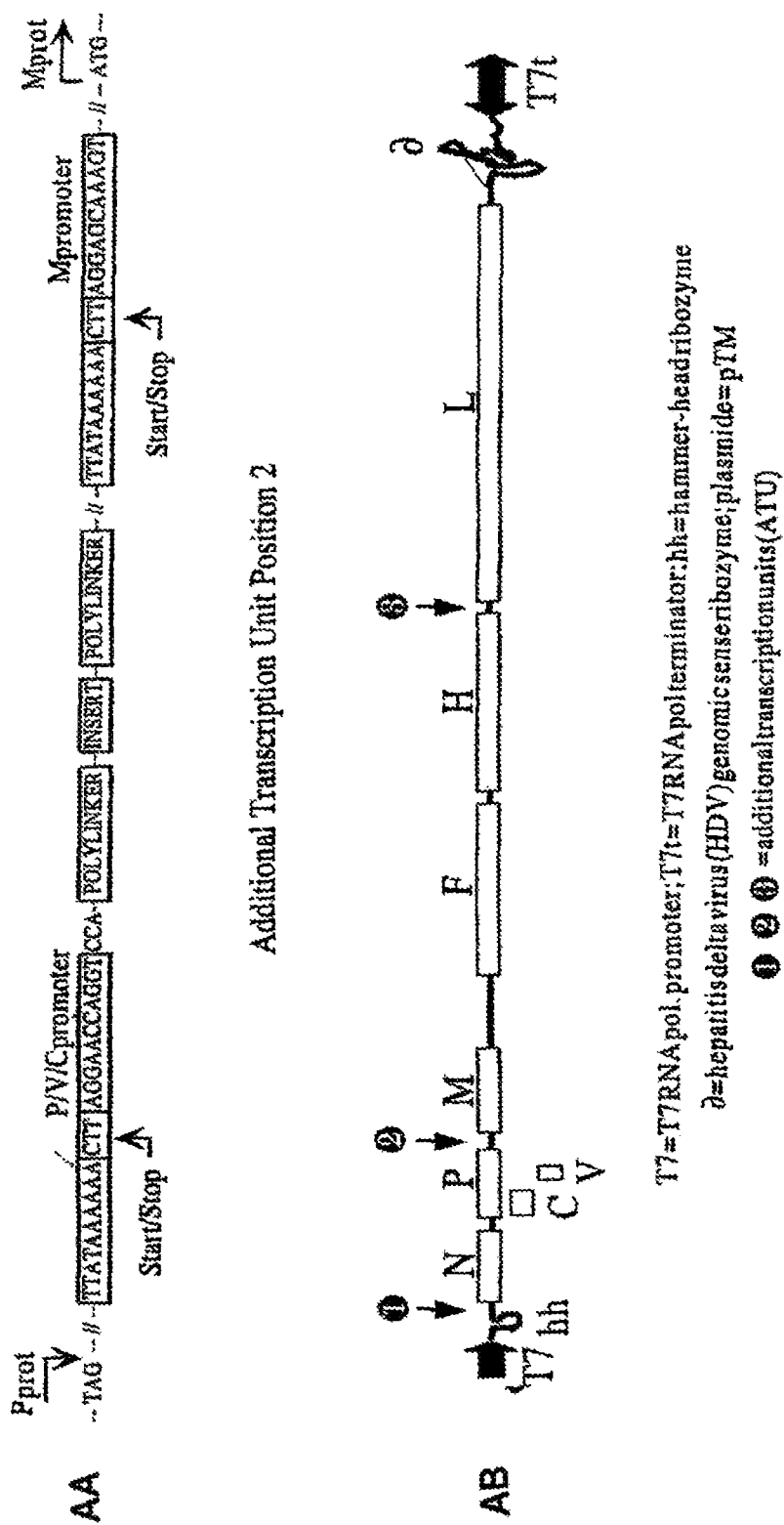

FIGS. 4A and 4B. A: Schematic representation the additional transcription unit (ATU) (SEQ ID NOS: 90 and 91) and Schwarz MV vector plasmid. (AA) Cis-acting elements of the ATU inserted in position 2 between phosphoprotein (P) and matrix (M) MV open reading frames. (AB). Representation of the three positions of ATU insertion in the Schwarz MV vector plasmid.

B: ATU sequence (SEQ ID NO: 83): small letters represent additional sequences (copy of the N-P intergenic region of measles virus) plus cloning sites. Capital letters correspond to the inserted enhanced GFP sequence. This sequence is inserted at the SpeI site (position 3373) of the cDNA sequence of the Schwarz strain of the measles virus for ATU2 and at the SpeI site (position 9174) for the ATU3. The mutation which distinguishes normal ATU from bis (in pTM-MVSchw2-gfp and pTM-MVSchw2-GFPbis) is a substituted C (Capital letter) at the end of ATU.

FIGS. 5A to 5G. Complete nucleotide sequence of the pTM-MVSchw plasmid (SEQ ID NO: 82). The sequence can be described as follows with reference to the position of the nucleotides:

1-8 NotI restriction site
9-28 T7 promoter
29-82 Hammer head ribozyme
83-15976 MV Schwarz antigenome
15977-16202 HDV ribozyme and T7 terminator
16203-16210 NotI restriction site
16211-16216 ApaI restriction site
16220-16226 KpnI restriction site
16226-18967 pBluescript KS(+) plasmid (Stratagene)

Figure 6:
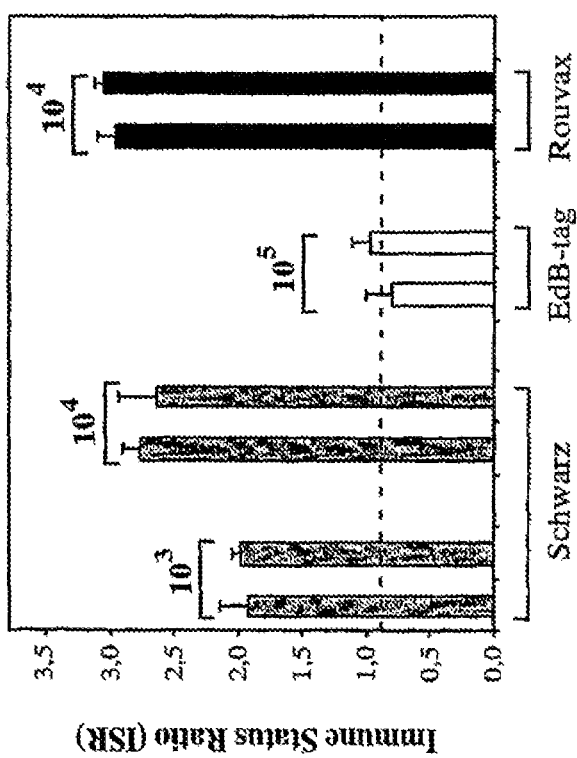

FIG. 6. Detection of anti-MV antibodies in macaques immunized with different MV vaccine strains. Anti-MV antibodies were detected by ELISA one month after immunization of rhesus macaques (2 monkeys per group) with Schwarz virus (gray bars), EdB-tag virus (white bars) and Rouvax vaccine (black bars) at the doses indicated. Immune status ratio (ISR) were calculated as described in materials and methods. Only ISR values higher than 0.9 were considered as positive (determinations were done in triplicate on 1/20 dilution of serum samples and results are expressed as the mean values±SD).

FIGS. 7A and 7B. Antibody titers to MV in mice immunized with different MV vaccine strains. Anti-MV antibodies were detected by ELISA one month after immunization of CD46 (A) and CD46/IFNAR (B) mice with $10^4$ $TCID_{50}$ of EdB-tag virus (white bars), Schwarz virus (gray bars) and Rouvax vaccine (black bars). Results are expressed as mean OD values±SD (4 mice per group) determined in serial dilutions of sera.

Figure 8:
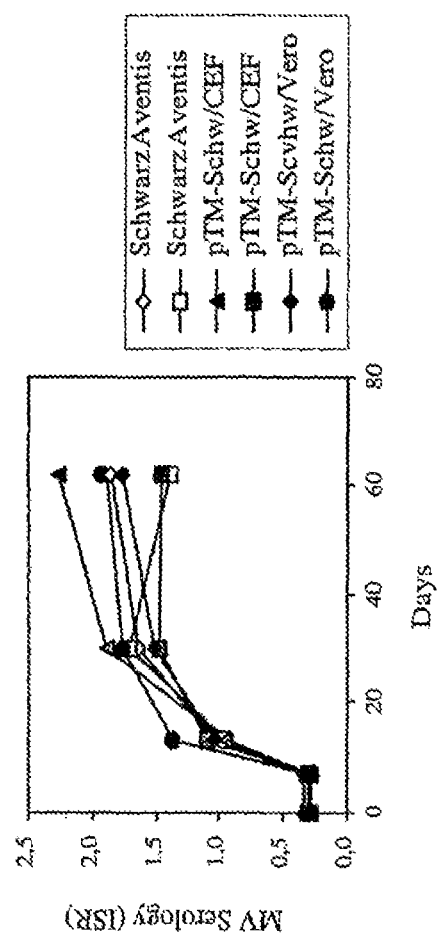
Figure 9A:
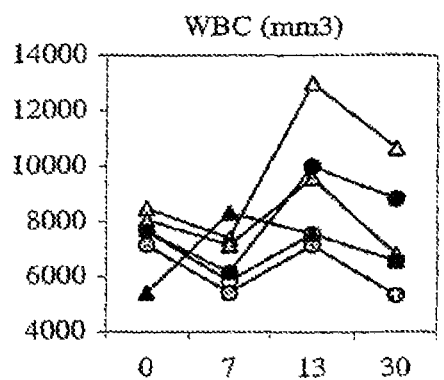
Figure 9B:
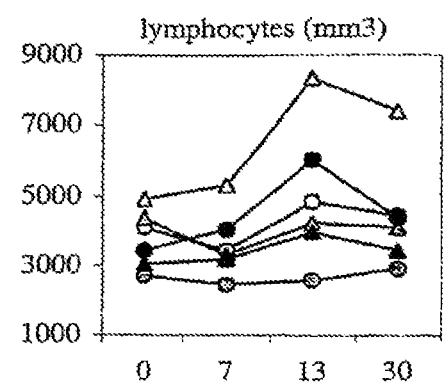
Figure 9C:
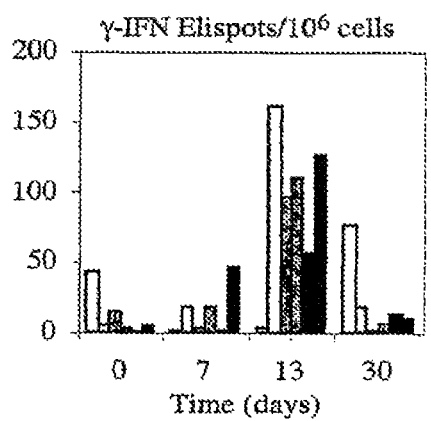
Figure 9D:
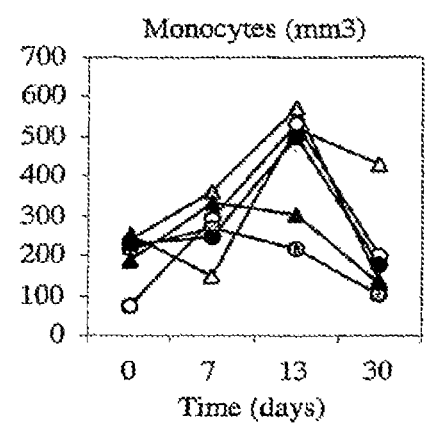

FIG. 8. Detection of anti-MV antibodies in macaques immunized with different Schwarz measles virus preparations. Anti-MV antibodies were detected by ELISA at different time points after immunization of cynomolgus macaques (2 monkeys per group) with $10^4$ $TCID_{50}$ of bulk industrial Schwarz virus (white marks), Schwarz virus rescued from pTM-MVSchw plasmid and grown on CEF (gray bars) or Vero cells (black bars). Immune status ratio (ISR) were calculated as described in materials and methods.

FIGS. 9A-9D. Changes in the number of circulating leukocytes and MV-specific T-cell response in macaques immunized with different Schwarz MV preparations. Enumeration of white blood cells (A), lymphocytes (B), monocytes (C), and MV hemaglutinin-specific IFN-γ-ELISpots (D) in PBMC of cynomolgus macaques collected at different time points after immunization with $10^4$ $TCID_{50}$ of bulk industrial Schwarz virus (white marks), Schwarz virus rescued from pTM-MVSchw plasmid and grown on CEF (gray bars) or Vero cells (black bars). IFN-γ-ELISpots were detected after stimulation of PBMC for 24 hours with a recombinant MVA expressing the MV hemaglutinin. The background obtained with MVA-wt stimulation was subtracted and the results are expressed as MVA-HMV specific γ-IFN producing cells per million PBMC.

FIGS. 10A and 10B. Schematic representation of the pTM-MVSchw-ATU plasmids (A) and GFP expression in Vero cells infected by rescued recombinant viruses (B). Vero cells were infected with recombinant Schwarz MV-GFP either in position ATU2 (left side) or position ATU3 (right side) and the GFP fluorescence was observed in syncytia.

EXAMPLES

Sequence Comparison Between EdB-Tag and Measles Vaccine Strains.

In a nice analysis previously reported (Parks, C. L., R. A. Lerch, P. Walpita, H. P. Wang, M. S. Sidhu, and S. A. Udem. 2001. Analysis of the noncoding regions of measles virus strains in the Edmonston vaccine lineage. J Virol. 75:921-933; Parks, C. L., R. A. Lerch, P. Walpita, H. P. Wang, M. S. Sidhu, and S. A. Udem. 2001. Comparison of predicted amino acid sequences of measles virus strains in the Edmonston vaccine lineage. J Virol. 75:910-920), the coding and non-coding sequences of Edmonston-derived vaccine virus strains were compared to that of a low-passage isolate of the Edmonston wild-type measles virus. The authors identified 10 amino acids substitutions shared by almost all the vaccine strains. We compared the genomic sequences of these Edmonston-derived vaccine strains and two primary isolates (Takeda, M., A. Kato, F. Kobune, H. Sakata, Y. Li, T. Shioda, Y. Sakai, M. Asakawa, and Y. Nagai. 1998. Measles virus attenuation associated with transcriptional impediment and a few amino acid changes in the polymerase and accessory proteins. J Virol. 72:8690-8696; Takeuchi, K., N. Miyajima, F. Kobune, and M. Tashiro. 2000. Comparative nucleotide sequence analyses of the entire genomes of B95a cell-isolated and vero cell-isolated measles viruses from the same patient. Virus Genes. 20:253-257) to that of the previously reported Edmonston B infectious cDNA (EdB-tag) (Radecke, F., P. Spielhofer, H. Schneider, K. Kaelin, M. Huber, K. Dötsch, G. Christiansen, and M. Billeter. 1995. Rescue of measles viruses from cloned DNA. EMBO Journal. 14:5773-5784). FIG. 1 shows that the nucleotide sequence of EdB-tag differed from that of Rubeovax (Edmonston B vaccine) by 0.24% (38 mutations) and from that of Schwarz/Moraten by 0.27% (44 mutations). Schwarz/Moraten and Emonston B (Rubeovax®) sequences differed only by 0.1% (16 mutations). Among the 38 differences between EdB-tag and Rubeovax, 17 were amino acid substitutions in coding regions and 7 were located in non-coding regions. Among the 44 differences between EdB-tag and Schwarz/Moraten, 22 were amino acid substitutions and 9 were in non-coding regions. The 10 amino acids substitutions shared by almost all the Edmonston vaccine strains Parks, C. L., R. A. Lerch, P. Walpita, H. P. Wang, M. S. Sidhu, and S. A. Udem. 2001. Analysis of the noncoding regions of measles virus strains in the Edmonston vaccine lineage. J Virol. 75:921-933; Parks, C. L., R. A. Lerch, P. Walpita, H. P. Wang, M. S. Sidhu, and S. A. Udem. 2001. Comparison of predicted amino acid sequences of measles virus strains in the Edmonston vaccine lineage. J Virol. 75:910-920) were conserved in EdB-tag cDNA. However, 5 of them were specific of the AIK-C and Zabreg subgroup, indicating that the virus from which EdB-tag was cloned diverged from Edmonston B and did not correspond to any approved vaccine strain. Moreover, 10 amino acid substitutions in EdB-tag were not related to any Edmonston subgroup, probably reflecting the adaptation to growth on HeLa cells and/or errors introduced during the cloning procedure. Among these specific changes, 5 were located in the P/V/C coding sequences and 3 were located in the L polymerase gene, thus possibly affecting the replicative capacity of the virus in vivo. These changes and others in cis-acting sequences may influence the immunogenicity or pathogenicity of the virus recovered from the EdB-tag cDNA. Indeed, MV adaptation to growth on Vero cells has been shown to be associated with loss of pathogenic potential (Kobune, F., H. Sakata, and A. Sugiura. 1990. Marmoset lymphoblastoid cells as a sensitive host for isolation of measles virus. J Virol. 64:700-705) and with a few amino acid changes located in the polymerase (L) and accessory (P/V/C) proteins resulting in transcriptional attenuation in lymphoid cells (Takeda, M., A. Kato, F. Kobune, H. Sakata, Y. Li, T. Shioda, Y. Sakai, M. Asakawa, and Y. Nagai. 1998. Measles virus attenuation associated with transcriptional impediment and a few amino acid changes in the polymerase and accessory proteins. J Virol. 72:8690-8696; Takeuchi, K., N. Miyajima, F. Kobune, and M. Tashiro. 2000. Comparative nucleotide sequence analyses of the entire genomes of B95a cell-isolated and vero cell-isolated measles viruses from the same patient. Virus Genes. 20:253-257.

Construction of a cDNA Corresponding to the Antigenome of the Schwarz Vaccine Strain of Measles Virus.

Figure 2:
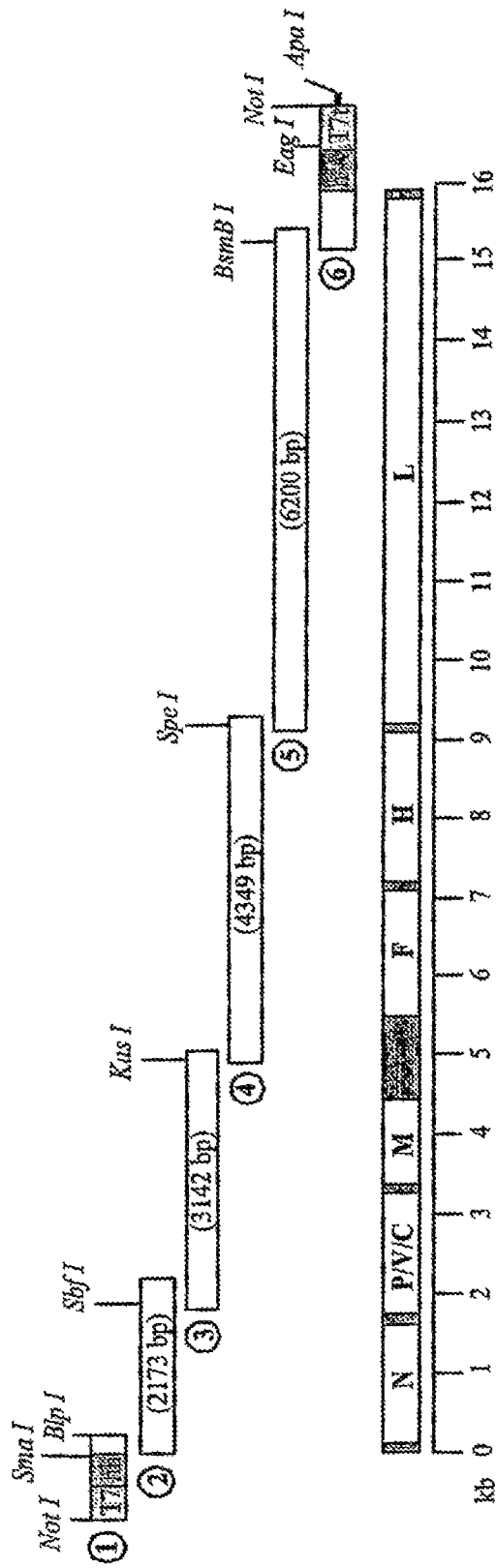
FIG. 2. Schematic map of the pTM-MV Schw plasmid. To construct the complete sequence, the six fragments represented in the upper part were generated and recombined step by step using the unique restriction sites indicated. T7=T7 promoter; hh=hammerhead ribozyme; hδv=hepatitis delta ribozyme; T7t=T7 RNA polymerase terminator. The following oligonucleotides were used for the sequencing of the MV Schwarz cDNA and the Schwarz MV rescued from the cDNA.

Viral particles were purified from a measles Schwarz vaccine batch kindly provided by Aventis Pasteur (Lyon, France). This bulk vaccine preparation (50 ml, 3 $10^4$ TCID$_{50}$/ml) was obtained by scraping of infected CEF cells, freeze-thawing cells and medium, and filtration of cellular debris. Particles were concentrated by centrifugation through a 30% sucrose cushion. Viral RNA was purified from lysed particles using a silica-gel-based membrane (QIAmp, Qiagen). Viral RNA was reverse-transcribed into cDNA using a mixture of random hexameres (pdN6, 1 µM) and a specific oligonucleotide representing the 32 first nucleotides of MV genome (MVSchwRT1 5'-ACCAAACAAAGTTGGGTAAGGATAGTTCAATC-3' (SEQ ID NO: 65), 10 µM), as primers. In order to ensure the fidelity of reverse transcription and the yield of full-length products, the SuperScript II DNA polymerase was used (GibcoBRL). A set of six overlapping fragments covering the full viral cDNA (numbered 1 to 6 in FIG. 2) were generated by PCR using PfuTurbo DNA polymerase (Stratagene) and a set of specific primers closed to unique restriction sites. Fragment 1 at the 5' end of the viral antigenome was engineered by PCR with specific primers in order to contain a T7 RNA polymerase promoter with the GGG motif necessary for a full efficiency and a hammerhead ribozyme sequence inserted between the T7 promoter and the first viral nucleotide. To generate this fragment, two overlapping oligonucleotides were annealed together:

Leader 1
(SEQ ID NO: 66)
(5'-TATGCGGCCGC<u>TAATACGACT</u>

<u>CACTATAGGG</u>CCAACTTTGTTTGGTCTGA-3')

containing a NotI site, the T7 promoter (underlined) and the 19 first nucleotides of hammerhead ribozyme sequence, and Leader 2 (5'-GGTGACCCGGGACTCCGGGTTTCGTCCTCACGGACTCATCAGACCAAACA-3') (SEQ ID NO: 67) containing the hammer head sequence with a SmaI/XmaI site. After PCR amplification, the resulting fragment was linked by PCR extension to a second fragment also generated by PCR from Schwarz cDNA using oligonucleotiaes MVSchw1
(SEQ ID NO: 68)
(5'-<u>GAGTCCCGGGTC</u>ACCAA ACAAAGTTGGGTAAG-3')

overlapping with hammerhead sequence (underlined) and covering MV Schwarz genome 1-15, and MVSchw160 (5'-GGTTTGTCCTTGTTTCTTTT-3' (SEQ ID NO: 69), MV Schwarz genome 141-160). Fragment 2 (2173 nucleotides long, see FIG. 2) was amplified using oligonucleotides MVSchwRT1 (5'-ACCAAACAAAGTTGGGTAAGGATAGTTCAATC-3' (SEQ ID NO: 70), MV Schwarz genome 1-32), and MVSchw2173 (5'-ATTCCCTTAACCGCTTCACC-3' (SEQ ID NO: 71), MV Schwarz genome 2155-2174). Fragment 3 (3142 nucleotides long) was amplified using oligonucleotides MV Schw1901 (5'-CTATGGCAGCATGGTCAGAAATA-3' (SEQ ID NO: 72), MV Schwarz genome 1901-1924) and MVSch5043 (5'-ATTGTCGATGGTTGGGTGCT-3' (SEQ ID NO: 73), MV Schwarz genome 5024-5043). Fragment 4 (4349 nucleotides long) was amplified using oligonucleotides MVSchw4869 (5'-AAACTTAGGGCCAAGGAACATAC-3' (SEQ ID NO: 74), MV Schwarz genome 4869-4891) and MVSchw9218 (5'-GGACCCTACGTTTTTCTTAATTCTG-3' (SEQ ID NO: 75), MV Schwarz genome 9194-9218). Fragment 5 (6200 nucleotides long) was amplified using oligonucleotides MVSchw9119 (5'-AGATAGGGCTGCTAGTGAACCAAT-3' (SEQ ID NO: 76), MV Schwarz genome 9119-9142) and MVSchw15319 (5'-ATCAGCACCTGCTCTATAGGTGTAA-3' (SEQ ID NO: 77), MV Schwarz genome 15295-15319). To obtain fragment 6, two overlapping fragments generated by PCR were annealed together. The following oligonucleotides were used: MVSchw15155 (5'-GCAGCAGATAATTGAATCATCTGTGAGGACTTCAC (SEQ ID NO: 78), MV Schwarz genome 15155-15190) and MVSchw15570 (5'-CCCGGAGTAAAGAAGAATGTGCCCCCAGAATTTGC-3' (SEQ ID NO: 79), MV Schwarz genome 15535-15570). This fragment was annealed to a fragment containing the hepatitis delta virus (HDV) ribozyme linked to the T7 terminator that was previously obtained by PCR amplification of p(MV+) plasmid (a kind gift from M. Billeter) using oligonucleotides MVSchw15547 (5'-GGCACATTCTTCTTTACTCCGGGAACAAAAAGTTG-3' (SEQ ID NO: 80), MV Schwarz genome 15547-15581) and MVSchwEnd (5'-ATAGGGCCCGCGGCCGCATCCGG ATATAGTTCCTCCTTTCA-3' (SEQ ID NO: 81) containing an ApaI restriction site linked to the last nucleotides of T7 terminator. The 6 fragments thus generated were cloned in pCR®2.1-TOPO® vector (Invitrogen, Groningen, Netherlands) and sequenced. In order to assemble the MV Schwarz full length DNA, a modified BlueScript KS (+) plasmid was constructed: two internally complementary oligonucleotides yielding a NotI, KasI/NarI, SpeI, ApaI polylinker were annealed and inserted in pTM plasmid digested with NotI/ApaI (pTM was derived from pBluescript KS (+) (Stratagene) by deletion of the T7 promoter (Tangy, F., A. McAllister, and M. Brahic. 1989. Molecular cloning of the complete genome of Theiler's virus, strain GDVII, and production of infectious transcripts. J. Virol. 63:1101-11066). The 6 MV Schwarz cDNA fragments were assembled together step by step using unique restriction sites. Fragments 1 and 2 were assembled together using BlpI site in MV sequence (FIG. 2) and BglII site in pCR®2.1-TOPO® vector backbone. The resulting plasmid was assembled with fragment 3 using SbfI site in MV sequence and BglII site in pCR®2.1-TOPO® vector backbone, yielding plasmid pCR®2.1-TOPO®-MVSchw-1-2-3 containing MV Schwarz fragments 1-3. After NotI/NarI digestion of this plasmid, the fragment containing the T7 promoter, hammer head ribozyme and the 4922 first nucleotides of MV Schwarz antigenome was inserted in NotI/NarI digested pTM vector, yielding pTM-MVL. At the same time, fragments 5 and 6 were assembled together using BsmBI site in MV sequence (FIG. 2) and BssHII site in pCR®2.1-TOPO® vector backbone, yielding plasmid pCR®2.1-TOPO®-MVSchw-5-6 containing MV Schwarz fragments 5-6. After SpeI/ApaI digestion of this plasmid, the fragment containing the 6720 last nucleotides of MV Schwarz antigenome, HDV ribozyme and T7 terminator sequences was inserted in SpeI/ApaI digested pTM vector, yielding pTM-MVT. For the final assembling, four fragments were prepared and ligated together: 1) a SapI/SapI fragment of pTM-MVL (4367 nucleotides long) containing a part of pTM backbone, the T7 promoter, hammer head ribozyme, and the 1813 first nucleotides of MV antigenome, 2) a SapI/NarI fragment of pTM-MVL (3110 nucleotides long) containing nucleotides 1813-4923 from MV Schwarz antigenome, 3) a NarI/SpeI fragment of pCR®2.1-TOPO®-MVSchw-3 (4253 nucleotides long) containing nucleotides 4923-12157 of MV Schwarz antigenome, and 4) a SpeI/SapI fragment of pTM-MVT (7235 nucleotides long) containing nucleotides 12157-15894 of MV Schwarz antigenome, HDV ribozyme, T7 terminator and a part of pTM vector backbone. After ligation and cloning, several full constructs were obtained. The resulting plasmid, named pTM-MVSchw, was fully sequenced (Acc. Num. CNCM I-2889). No mutation was found between this cDNA and the previously reported sequence of Schwarz genome (Parks, C. L., R. A. Lerch, P. Walpita, H. P. Wang, M. S. Sidhu, and S. A. Udem. 2001. Analysis of the noncoding regions of measles virus strains in the Edmonston vaccine lineage. J Virol. 75:921-933; Parks, C. L., R. A. Lerch, P. Walpita, H. P. Wang, M. S. Sidhu, and S. A. Udem. 2001. Comparison of predicted amino acid sequences of measles virus strains in the Edmonston vaccine lineage. J Virol. 75:910-920).

Recovery of Infectious Schwarz Virus from pTM-MVSchw Plasmid.

To recover the Schwarz virus from the pTM-MVSchw cDNA, we used the helper-cell-based rescue system described by Radecke et al. (Radecke, F., P. Spielhofer, H. Schneider, K. Kaelin, M. Huber, K. Dötsch, G. Christiansen, and M. Billeter. 1995. Rescue of measles viruses from cloned DNA. EMBO Journal. 14:5773-5784) and modified by Parks et al. (Parks, C. L., R. A. Lerch, P. Walpita, M. S. Sidhu, and S. A. Udem. 1999. Enhanced measles virus cDNA rescue and gene expression after heat shock. J Virol. 73:3560-3566). Human helper cells stably expressing T7 RNA polymerase and measles N and P proteins (293-3-46 cells, disclosed by Radecke et al (17) were transfected using the calcium phosphate procedure with pTM-MVSchw plasmid (5 μg) and a plasmid expressing the MV polymerase L gene (pEMC-La, 20 ng, disclosed by Radecke et al (17). After overnight incubation at 37° C., the transfection medium was replaced by fresh medium and a heat shock was applied (43° C. for two hours) (12). After two days of incubation at 37° C., transfected cells were transferred on a CEF cells layer and incubated at 32° C. in order to avoid any adaptation of the Schwarz vaccine that was originally selected on CEF cells and is currently grown on these cells for safety considerations. The above chicken embryo fibroblastic cells (CEF) were prepared as follows. Fertilized chicken eggs (EARL Morizeau, 8 rue Moulin, 28190 Dangers, France) was incubated at 38° C. for 9 days. Embryos were collected sterilely. Head, limbs and viscera were removed and embryos were sliced up and trypsinized for 5-10 minutes at 37° C. (Trypsine/EDTA 2.5 g/L). After filtration (70 μm) and several washes in DMEM high glucose/10% FCS, cells were seeded (5-7 $10^6$ cells/pertri dish) and incubated overnight at 37° C. Infectious virus was easily recovered between 3 and 7 days following cocultivation. Syncytia appeared occasionally in CEF, but not systematically. The Schwarz virus was also rescued by the same technique after cocultivation of transfected 293-3-46 helper cells at 37° C. with primate Vero cells (african green monkey kidney). In this case, syncytia appeared systematically in all transfections after 2 days of coculture. In order to test for viral adaptation to Vero cells, a preparation of cloned Schwarz virus rescued on Vero cells was passaged two times on Vero cells. Viral particles were purified and viral RNA was reverse-transcribed as described above with the primers used for the cloning (see above). The viral genome was fully sequenced. Two nucleotide changes out of 15894 were found between the rescued/passaged virus and the cDNA used for transfection. These mutations were found in 7 and 8 respectively out of 10 different clones of the same region, indicating a high percentage of mutation among the viral population. Moreover, both mutations resulted in amino acid changes in the fusion protein (F): G→R in position 266 and Y→S in position 365.

In contrast, the genomic sequence of the virus recovered and passaged on CEF cells at 32° C. was identical to that of the original Schwarz virus. This observation indicates that changing the host cell of Schwarz virus leads to a rapid adaptation that may affect the properties of the vaccine.

Growth Capacity of the Rescued Virus.

The capacity of the Schwarz virus rescued from cDNA to grow on CEF and Vero cells was analyzed and compared to the industrial bulk Schwarz vaccine from which it was derived (obtained from Aventis Pasteur) and to the EdB-tag virus rescued from its cDNA. Monolayers of Verocells in 6-well plates were infected with viruses at different multiplicity of infection. A various time post infection (pi), the cells were seraped into culture medium. After freezing and thawing, infectivity titers were determined by measuring the $TCID_{50}$ in Vero cells. Growth curves: Monolayers of Vero cells in 6-well plates were infected with viruses at different multiplicities of infection (MOI). At various times postinfection (pi), the cells were scraped into culture medium. After freezing and thawing, infectivity titers were determined by measuring the $TCID_{50}$ in Vero cells.

$TCID_{50}$ Titration:

Vero cells were seeded into 96-well plate (7500 cells/well) and infected by serial 1:10 dilutions of virus sample in DMEM/5% FCS. After incubation at 37° C. for 4-5 days for Ed-B virus and 7 days for Schwarz virus, cells were stained with crystal violet and the virus dilution that resulted in infection in 50% of test unit was determined. The 50% end point described as tissue culture infectious dose ($TCID_{50}$) was calculated by the Kärber method (Karber, G. 1931. Beitrag zur kollektiven Behandlung pharmakologischer Reihenversuche. Arch Exp Path Pharmak. 162:480-483). Tested on Vero cells, the growth kinetics of Schwarz and EdB-tag viruses rescued from their respective cDNA were similar (FIG. 3). The Schwarz viral production on Vero cells reached high yields ($10^7$-$10^8$ $TCID_{50}$/ml after two days of infection using a multiplicity of infection of 0.01). Tested on CEF cells, the Schwarz virus was able to grow as well at 32° C. as at 37° C., while the EdB-tag was not (FIG. 3). This observation confirms that the virus from which EdB-tag was cloned was not adapted to CEF cells. The yield of Schwarz virus on CEF was lower than on Vero cells ($10^6$ $TCID_{50}$/ml after 4 days of infection using a multiplicity of infection of 0.05). Similar growth curves and similar titers were observed when CEF cells were infected with the original Schwarz virus from which it was cloned (FIG. 3). These observations demonstrate that the Schwarz virus rescued from its cDNA had the same growth characteristics than the original vaccine batch from which it was cloned.

Introduction of an Additional Transcription Unit in the Schwarz cDNA.

In the previous work reporting the cloning of EdB-tag virus (17), the authors developed an original method to adapt the viral cDNA as a vector suitable for the expression of foreign transgenes. They inserted an additional transcription unit (ATU) in different positions of the viral genome. This ATU is a copy of the MV N-P intergenic region containing the cis-acting sequences necessary for MV-dependant expression of a transgene inserted into a multiple cloning sites cassette. Largely tested by the authors and ourselves, the expression of foreign transgenes inserted in this ATU was very efficient, depending on the position of insertion in the genome. The different MV genes are expressed according to a transcriptional gradient down the genome, leading to a high expression of the N gene to a low expression of the L gene (Lamb, R., and D. Kolakofsky. 1996. Paramyxoviridae: the viruses and their replication, p. 1177-1199. In B. Fileds, D. Knipe, et al. (ed.), Fields Virology. Lippincott-Raven Publishers, Philadelphia).

The insertion of the ATU takes advantage of this gradient, allowing high or low expression of the transgene, depending on the position of insertion. Moreover, in this context the foreign transgenes are expressed using the same controls and pathways as authentic MV genes.

In order to transform the Schwarz cDNA as a vector, we constructed a similar ATU that was inserted in two different positions of the cDNA (FIG. 4). The cDNA was sequenced and no mutation was found.

Immunogenicity of Schwarz MV Recovered from cDNA in Macaques.

First Experiment: Comparison with Schwarz Vaccine.

The immunogenicity of the virus rescued from pTM-MVSchw plasmid and passaged two times on CEF cells was compared to the immunogenicity of Schwarz vaccine in cynomolgus macaques. The conditions for passage were the following:

After rescue, isolated syncytia were picked from the CEF cells cocultivated with 293-3-46 helper cells and a single syncytium was diluted in 600 μl of OptiMEM 1 (Gibco) and vortexed. This inoculum was used to infect fresh CEF cells (80-90% confluent) in a 35 mm well or a T-25 flask. After 2 hours of adsorption at 37° C., the inoculum was replaced by DMEM/5% FCS and cells were incubated at 32° C. for 1-2 days. When small syncytia appeared, infected cells were expanded to T-75 flasks: cells were washed with PBS and detached with PBS/1 mM EDTA/0.25% trypsin for 1 minute, then transferred to T-75 flasks together with fresh CEF cells (¼ of a confluent T-75 flask culture). After 4-7 days of incubation at 32° C. in DMEM/5% FCS, the virus (passage 1) was harvested: culture medium was removed and infected cells were scraped in 3 ml of OptiMEM 1. After one cycle of freezing and thawing, cell debris were discarded by centrifugation (1500 rpm, 5 minutes, room temperature). This stock seed was kept frozen at −80° C. and used to infect fresh CEF in the same way to prepare the passage 2 stock.

Different formulations of the vaccine were tested using both the unpassaged bulk preparation from Aventis Pasteur, and the same preparation passaged two times on CEF cells. Viruses were prepared as follows: CEF cells (obtained from chick embryos incubated during 9 days) were infected at a MOI of 0.05 and incubated at 32° C. during 7 days. Viruses were purified by scraping infected cells, freeze/thawing and low speed clarification of cells debris. Stabilizing agents used in the preparation of MV vaccine were obtained from Aventis Pasteur. Different bulk vaccine preparations with and without stabilizing agents were compared at the same dose to the lyophilized final product (Rouvax, Aventis Pasteur). All vaccine preparations were titrated using the $TCID_{50}$ method on Vero cells. Monkeys were injected subcutaneously and blood samples were taken at different time points. In order to compare both humoral and cellular responses, the presence of anti-MV antibodies was looked for in serums by ELISA (Trinity Biotech, USA) and the presence of anti-MV T-cells was looked for by ELISPOT in PBMCs.

Second Experiment: Comparison with EdB-Tag Strain

Colony-bred rhesus (*Macaca mulatta*) or cynomolgus (*Macaca fascicularis*) macaques that were seronegative for simian type D retrovirus, simian T-cell lymphotropic virus, simian immunodeficiency virus, and measles virus were housed in accordance with the American Association for Accreditation of Laboratory Animal Care. Monkeys were inoculated subcutaneously with different doses ($10^3$-$10^5$ $TCID_{50}$) of EdB-tag or Schwarz MV diluted in OptiMEM (GibcoBRL) or with $10^4$ $TCID_{50}$ of the lyophilized Rouvax MV vaccine (Aventis Pasteur, Marcy l'Etoile, France) diluted in the solution provided by the supplier. Blood samples were collected at different time after inoculation.

The presence of anti-MV antibodies in serum was looked for by ELISA (Trinity Biotech, USA) one month after vaccination. Each determination was done in triplicate on 1/20 dilution of serum samples. A mixture of 5 samples from negative monkeys was used as the negative control. To determine the immune status ratio (ISR) of each sample, the absorbance of the negative control was subtracted from the absorbance of the positive sample and the result was divided by the absorbance of a calibrator supplied in the ELISA kit, as recommended by the supplier. Only ISR values higher than 0.9 were considered as positive in this test.

Cellular immune responses were determined by γ-IFN ELISpot assays. Frozen PBMC were thawed and incubated overnight in RPMI, 10% FCS and 4 U/ml rh-IL2 (Boehringer Mannheim). Multiscreen-HA 96-wells plates were coated overnight at 4° C. with 4 μg/ml of capture anti-γ-IFN (GZ-4, MAbTech) in PBS, washed, then incubated with 100 μl RPMI, 10% FCS for 1 h at 37° C. The medium was replaced by $5 \cdot 10^5$ PBMC in suspension in 100 μl of RPMI-10% FCS and 100 μl of stimulating agent. The stimulating agent consisted of $10^7$ pfu of recombinant Modified Vaccine Ankara (32) MVA-$H_{MV}$ or MVA-wt as a control Cells were stimulated for 24 h at 37° C. Phytohemaglutinin A (2.5

μg/ml, Sigma) was used as positive control and RPMI as a negative control. The plates were washed twice with PBS, 4 times with PBS, 0.05% Tween 20 (Sigma), and twice again with PBS. A biotinylated anti-γ-IFN antibody (7-66-1, MabTech, 100 μl, 1 μg/ml in PBS) was added and the plates were incubated for 2-4 h at 37° C. Streptravidin-Alkaline Phosphatase (AP) conjugate (Roche, 100 μl, 1/2000 dilution in PBS) was added And spots were developed with BCIP/NBT (Promega) in 1 M Tris pH 9.5, 1.5 M NaCl, 0.05 M MgCl2. After drying overnight at room temperature, spots were counted using an automated image analysis system (ELISpot Reader, Bio-Sys). The low background obtained after MVA-wt stimulation was subtracted and the results were expressed as MVA-$H_{MV}$ specific γ-IFN producing cells per million PBMC.

Mice immunization and characterization of humoral immune responses. FVB mice heterozygous for the CD46 transgene (33), were crossed with 129sv IFN-α/βR$^{-/-}$ mice which lack the type I interferon receptor (30). The F1 progeny was screened by PCR and the CD46$^{+/-}$ animals were crossed again with 129sv IFN-α/βR$^{-/-}$ mice. IFN-α/βR$^{-/-}$ CD46$^{+/-}$ animals were selected and used for immunization experiments. These mice are susceptible to MV infection (27, 29). Six-week-old female CD46$^{+/-}$ or CD46$^{+/-}$ IFN-α/βR$^{-/-}$ (IFNAR) mice were inoculated intraperitoneally with $10^4$ TCID$_{50}$ of the different vaccine preparations (4 mice per group). The presence of anti-MV antibodies was looked for by ELISA (Trinity Biotech, USA) in sera collected one month after vaccination. In this case, an anti mouse IgG Mab (Amersham) was used as secondary antibody. Each determination was done in triplicate. The absorbence determined with a mixture of negative mice sera was subtracted from the absorbence measured in positive mice. Because it was not possible in this case to use the ISR to compare samples, serial dilutions of mice sera were tested to determine the endpoint limit positive dilution.

Results

Comparison of Humoral Immune Responses after Vaccination of Macaques and Mice with EdB-Tag and Schwarz MV Vaccines.

EdB-tag MV is a molecularly cloned MV derived from the Edmonston B strain (16). We compared its immunogenicity in macaques with that of the Schwarz commercial MV vaccine. The EdB-tag virus was prepared in Vero cells infected at a multiplicity of infection (MOI) of 0.05. When syncytia occupied 80-90% of the culture, the cells were scraped, cells and medium were freeze/thawed and cell debris were eliminated by low speed centrifugation. The Schwarz MV, obtained from Aventis Pasteur (Marcy l'Etoile, France), was prepared in the same way from infected chick embryo fibroblasts (CEF) grown at 32° C., the temperature at which this strain has been adapted to CEF. The titers of both vaccine preparations were determined by endpoint dilution assays in Vero cells and expressed as TCID$_{50}$. Different doses ($10^3$ to $10^5$ TCID$_{50}$) of EdB-tag and Schwarz MV were injected subcutaneously to macaques (2 monkeys per dose). As a control, animals were also injected with $10^4$ TCID$_{50}$ of the lyophilized commercial Schwarz vaccine (Rouvax, Aventis Pasteur). Anti-MV antibodies levels were determined by ELISA in macaques' sera collected one month after vaccination. Macaques inoculated with $10^3$ and $10^4$ TCID$_{50}$ of the Schwarz MV had antibody levels similar to those induced by a standard dose of Rouvax vaccine (FIG. 6). Macaques inoculated with $10^4$ TCID$_{50}$ of EdB-tag virus remained negative (not shown). The injection of a tenfold higher dose ($10^5$ TCID$_{50}$) induced only a weak response that was lower than that observed with $10^3$ TCID$_{50}$ of Schwarz MV (FIG. 6). Vaccination with the commercial vaccine induced the best response probably due to the adjuvant effect of lyophilization.

Figure 7:
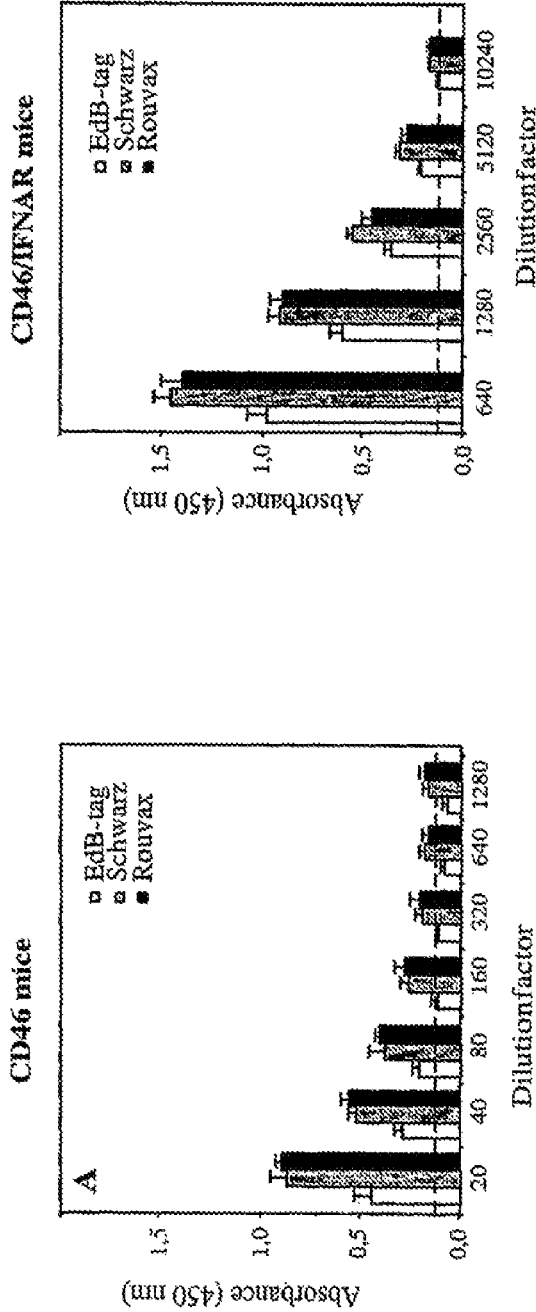

The different vaccine preparations were also tested in genetically modified mice obtained as described in Materials and Methods. Two types of mice were used: mice expressing CD46 (33), the human receptor for MV vaccine strains (34), and mice expressing CD46 and lacking the IFN type I receptor (29). Six-week-old mice were inoculated intraperitoneally with $10^4$ TCID$_{50}$ of the different vaccine preparations (4 mice per group). FIG. 7 shows the detection of anti-MV antibodies in sera of both types of mice collected one month after vaccination. In CD46 mice, the EdB-tag virus was less immunogenic than the Schwarz vaccine. The average titer obtained with the former was 1/80, whereas it was 1/1280 with the latter. The EdB-tag virus was also less immunogenic in CD46 mice lacking the IFN type I receptor but the difference was less pronounced than in CD46 immuno-competent mice, possibly indicating a difference in sensitivity to IFN α/β between the two viral strains.

Immunogenicity of Schwarz MV Recovered from cDNA.

The immunogenicity for cynomolgus macaques of the virus rescued from pTM-MVSchw plasmid and passaged two times on CEF or Vero cells was compared to that of the industrial Schwarz vaccine. Cynomolgus macaques were used in this experiment because of the difficulty of obtaining rhesus macaques from China that were MV negative. These macaques are as sensitive to MV as rhesus macaques, as shown by several studies (28, 26). Monkeys (2 animals per preparation) were injected sub-cutaneaously with $10^4$ TCID$_{50}$ of Schwarz MV vaccine from Aventis or Schwarz MV rescued from pTM-MVSchw plasmid and grown either on CEF or Vero cells. The presence of anti-MV antibodies was determined in sera collected at different time points (FIG. 8). All the vaccinated macaques became positive. No statistically significant difference was observed, one or two months after immunization, between the different vaccine preparations tested. This result demonstrates that the virus rescued from the pTM-MVSchw plasmid has the same immunogenicity in non human primates as the parental Schwarz vaccine. No difference was detected between the rescued viruses grown on CEF or Vero cells, indicating that the two mutations generated in the F protein by the passages on Vero cells did not affect the immunogenicity of the virus.

Changes in the number of total white blood cells (WBC), lymphocytes and monocytes were observed during the first month following inoculation (FIG. 9). There was a mild leukopenia during the first week, as previously observed after MV vaccination (1). During the second week a clear increase in the number of circulating lymphocytes and monocytes was observed. It coincided with a peak of the number of MV-specific T-lymphocytes as detected by a γ-IFN ELISpot assay (FIG. 9 D). No statistically significant difference was detected between the specific cellular immune responses induced by the Schwarz MV rescued from plasmid and the Schwarz vaccine prepared by Aventis.

DISCUSSION

In the present work we describe cloning and rescuing the Schwarz/Moraten attenuated strain of measles virus, the constituent of two widely used measles vaccines, Attenuavax (Merck and Co. Inc., West Point, USA) and Rouvax (Aventis Pasteur, Marcy l'Etoile, France), and of the combined measles, mumps, and rubella vaccine (MMR) (35). To be used in a pediatric clinical trial, a live attenuated MV produced from a cDNA must be as safe and efficient as the parental vaccine. Assuming that safety and efficiency depend ultimately on the genomic sequence of the attenuated strain, we cloned the MV Schwarz cDNA from viral particles prepared from an industrial batch of vaccine using procedures optimized for fidelity of cloning. As a result, the sequence of the clone that we obtained was identical to that of the parental Schwarz MV genome. To maximize yield during rescue, the viral antigenomic cDNA was placed under the control of a T7 RNA polymerase promoter with the GGG motif necessary for full efficiency. A hammerhead ribozyme was inserted between this GGG motif and the first viral nucleotide to allow the exact cleavage of the viral RNA. In order to avoid adapting the Schwarz vaccine to non-certified cells during rescue, helper cells transfected with the engineered cDNA were cocultivated with CEF, the cells on which this vaccine was selected originally and is currently prepared. The rescued virus was passaged two times on CEF and its genome was entirely sequenced. No mutation was found when the sequence was compared to that of the original virus. Moreover, the growth kinetics and the yield of the rescued virus and the original Schwarz virus on CEF were identical.

The Schwarz virus was also rescued after co-cultivation of transfected helper cells with Vero cells, which are very permissive to MV. In this case, however, two mutations appeared in the viral fusion protein (F) after two passages on Vero cells. This rapid adaptation correlated with a much more fusogenic phenotype on Vero cells. In contrast, the rescued Schwarz MV was not fusogenic on CEF (only rare syncytia could be observed in infected CEF). The two mutations occurred in the F protein (G→R in position 266 and Y→S in position 365). These mutations are present in the EdB-tag virus (see FIG. 6) which is grown on Vero cells. They are also present in the Hallé strain, which is highly related to Edmonston strain and does not infect CEF (31). These two mutations appear thus to correlate with enhanced fusion in Vero cells. The rapid adaptation of the F protein after only two passages of the Schwarz virus on Vero cells shows that in order to keep its genetic integrity the vaccine must be grown on CEF.

The virus rescued from the pTM-Schw plasmid had the same immunogenicity in macaques as the parental Schwarz vaccine. It is important to emphasize that in these experiments macaques were inoculated with the low dose of virus used for human immunization. Therefore, it will be possible to conduct human clinical trials with this virus using standard vaccine doses ($10^4$ TCID$_{50}$). In contrast, the previously cloned EdB-tag MV was not immunogenic in macaques and poorly immunogenic in mice transgenic for CD46, when used at the same dose as the cloned Schwarz MV.

What could be the reason for the higher immunogenicity of the Schwarz MV strain? Inducing good immunogenicity with a live attenuated viral vaccine requires replication in tissues at a level high enough to prime the immune system adequately. Several of the mutations between the Schwarz and the EdB-tag MV genomes are located in the P/V/C and L genes, suggesting difference in replication efficiency. It is possible that the Schwarz MV replicates in lymphoid cells in vivo more efficiently than the EdB-tag MV even though they replicated at the same rate in Vero cells. Efficient replication in vivo requires some evasion mechanism from the IFN-α/β response. Vero cells, on which the EdB-tag virus was adapted, do not respond to IFN-α/β stimulation. Therefore the EdB-tag MV was selected in the absence of an IFN-α/β response and might be particularly sensitive to this host defense mechanism. Indeed, it has been shown that passaging wild type MV on Vero cells changes the phenotype of the virus from non-IFN-inducer to IFN-inducer (36). Also, the fact that the Ed-tag MV was immunogenic in mice transgenic for the CD46 receptor providing they were also knock-out for the IFN-α/β receptor suggest that this virus is particularly IFN-sensitive. Interestingly, the IFN-α/β response helps priming the specific immune response against the vaccine. Therefore a good live vaccine must at the same time induce an IFN-α/β response and evade it to some extent. For this reason selecting attenuated viral vaccines on primary cells with a strong IFN-α/β response, such as CEF, might be a good strategy.

The MV products which contribute to IFN resistance have not been identified. However, the nonstructural C protein of the closely related Sendai virus has been shown to counteract the IFN-induced antiviral state (37). The 5 mutations not related to any Edmonston subgroup that we found in the EdB-tag P/V/C gene might be responsible for its low immunogenicity in macaques. On the other hand, the two mutations generated in the F protein by passaging the Schwarz virus on Vero cells did not affect its immune potential, indicating that the fusogenic property of the viral envelope proteins may not play a significant role in immunogenicity.

The pTM-MVSchw plasmid was engineered for the expression of foreign genes by the introduction of two ATU at different positions of the genome. Rescued Schwarz recombinant MV expressed the green fluorescent protein, thus showing that this new measles vaccine functions as a vector. In conclusion, this molecular clone will allow producing MV vaccine without having to rely on seed stocks. With its ATUs, it will be possible to use it as a vector to produce recombinant vaccines based on an approved, efficient and worldwide used vaccine strain.

BIBLIOGRAPHY

1. Andino, R., D. Silvera, S. D. Suggett, P. L. Achacoso, C. J. Miller, D. Baltimore, and M. B. Feinberg. 1994. Engineering poliovirus as a vaccine vector for the expression of diverse antigens. Science. 265:1448-1451.
2. Ballart, I., D. Eschle, R. Cattaneo, A. Schmid, M. Metzler, J. Chan, S. Pifko-Hirst, S. A. Udem, and M. A. Billeter. 1990. Infectious measles virus from cloned cDNA. Embo J. 9:379-384.
3. Crotty, S., C. J. Miller, B. L. Lohman, M. R. Neagu, L. Compton, D. Lu, F. X. Lu, L. Fritts, J. D. Lifson, and R. Andino. 2001. Protection against simian immunodeficiency virus vaginal challenge by using Sabin poliovirus vectors. J Virol. 75:7435-7452.
4. Enders, J. F., and T. C. Peebles. 1954. Propagation in tissue cultures od cytopathogenic agents from patients with measles. Proc. Soc. Exp. Biol. Med. 86:277-286.
5. Felsenstein, J. 1989. Cladistics. 5:164-166.
6. Griffin, D., and W. Bellini. 1996. Measles virus, p. 1267-1312. In B. Fields, D. Knipe, et al. (ed.), Virology, vol. 2. Lippincott—Raven Publishers, Philadelphia.
7. Hilleman, M. 2002. Current overview of the pathogenesis and prophylaxis of measles with focus on practical implications. Vaccine. 20:651-665.
8. Kobune, F., H. Sakata, and A. Sugiura. 1990. Marmoset lymphoblastoid cells as a sensitive host for isolation of measles virus. J Virol. 64:700-705.

9. Lamb, R., and D. Kolakofsky. 1996. Paramyxoviridae: the viruses and their replication, p. 1177-1199. In B. Fileds, D. Knipe, et al. (ed.), Fields Virology. Lippincott-Raven Publishers, Philadelphia.
10. Page, R. D. 1996. TreeView: an application to display phylogenetic trees on personal computers. Comput Appl Biosci. 12:357-358.
11. Palese, P. 1998. RNA virus vectors: where are we and where do we need to go? Proc Natl Acad Sci USA. 95:12750-12752.
12. Parks, C. L., R. A. Lerch, P. Walpita, M. S. Sidhu, and S. A. Udem. 1999. Enhanced measles virus cDNA rescue and gene expression after heat shock. J Virol. 73:3560-3566.
13. Parks, C. L., R. A. Lerch, P. Walpita, H. P. Wang, M. S. Sidhu, and S. A. Udem. 2001. Analysis of the noncoding regions of measles virus strains in the Edmonston vaccine lineage. J Virol. 75:921-933.
14. Parks, C. L., R. A. Lerch, P. Walpita, H. P. Wang, M. S. Sidhu, and S. A. Udem. 2001. Comparison of predicted amino acid sequences of measles virus strains in the Edmonston vaccine lineage. J Virol. 75:910-920.
15. Racaniello, V. R., and D. Baltimore. 1981. Cloned poliovirus complementary DNA is infectious in mammalian cells. Science. 214:916-919.
16. Radecke, F., and M. Billeter. 1997. Reverse genetics meets the nonsegmented negative-strand RNA viruses. Reviews in Medical Virology. 7:49-63.
17. Radecke, F., P. Spielhofer, H. Schneider, K. Kaelin, M. Huber, K. Dötsch, G. Christiansen, and M. Billeter. 1995. Rescue of measles viruses from cloned DNA. EMBO Journal. 14:5773-5784.
18. Singh, M., and M. Billeter. 1999. A recombinant measles virus expressing biologically active human interleukin-12. J. Gen. Virol. 80:101-106.
19. Singh, M., R. Cattaneo, and M. Billeter. 1999. A recombinant measles virus expressing hepatitis B virus surface antigen induces humoral immune responses in genetically modified mice. J. Virol. 73:4823-4828.
20. Spielhofer, P., T. Bachi, T. Fehr, G. Christiansen, R. Cattaneo, K. Kaelin, M. Billeter, and H. Naim. 1998. Chimeric measles viruses with a foreign envelope. J. Virol. 72:2150-2159.
21. Takeda, M., A. Kato, F. Kobune, H. Sakata, Y. Li, T. Shioda, Y. Sakai, M. Asakawa, and Y. Nagai. 1998. Measles virus attenuation associated with transcriptional impediment and a few amino acid changes in the polymerase and accessory proteins. J Virol. 72:8690-8696.
22. Takeuchi, K., N. Miyajima, F. Kobune, and M. Tashiro. 2000. Comparative nucleotide sequence analyses of the entire genomes of B95a cell-isolated and vero cell-isolated measles viruses from the same patient. Virus Genes. 20:253-257.
23. Tangy, F., A. McAllister, and M. Brahic. 1989. Molecular cloning of the complete genome of Theiler's virus, strain GDVII, and production of infectious transcripts. J. Virol. 63:1101-1106.
24. Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-4680.
25. Wang, Z., T. Hangartner, L. Cornu, A. Martin, M. Zuniga, M. Billeter, and H. Naim. 2001. Recombinant measles viruses expressing heterologus antigens of mumps and simian immunodeficiency viruses. Vaccine. 19:2329-2336.
26. Van Binnendijk, R. S., R. W. J. van der Heijden, G. van Amerongen, F. UytdeHaag, and A. D. M. E. Osterhaus. 1994. Viral replication and development of specific immunity in macaques after infection with different measles virus strains. The Journal of infectious Diseases. 170:443-448.
27. Mrkic, B., B. Odermatt, M. Klein, M. Billeter, J. Pavlovic, and R. Cattaneo. 1999. Lymphatic dissemination and comparative pathology of recombinant measles viruses in genetically modified mice. Journal of Virology. 74:1364-1372.
28. Kobune, F., H. Takahashi, K. Terao, T. Ohkawa, Y. Ami, Y. Suzaki, N. Nagata, H. Sakata, K. Yamanouchi, and C. Kai. 1996. Nonhuman primate models if measles. Laboratory Animal Science. 46:315-320.
29. Mrkic, B., J. Pavlovic, T. Rulicke, P. Volpe, C. J. Buchholz, D. Hourcade, J. P. Atkinson, A. Aguzzi, and R. Cattaneo. 1998. Measles virus spread and pathogenesis in genetically modified mice. J Virol. 72:7420-7427.
30. Müller, U., U. Steinhoff, L. F. L. Reis, S. Hemmi, J. Pavlovic, R. M. Zinkernagel, and M. Aguet. 1994. Functional role of type I and type II interferons in antiviral defense. Science. 264:1918-1921.
31. Escoffier, C., and D. Gerlier. 1999. Infection of chicken embryonic fibroblasts by measles virus: adaptation at the virus entry level. J Virol. 73:5220-5224.
32. Koert J. Stittelaar, Linda S. Wyatt, Rik L. de Swart, Helma W. Vos, Jan Groen, Geert van Amerongen, Robert S. van Binnendijk, Shmuel Rozenblatt, Bernard Moss, and Albert D. M. E. Osterhaus. May 2000. Protective immunity in macaques vaccinated with a modified vaccinia virus ankara-based measles virus vaccine in the presence of passively acquired antibodies. Journal of Virology. Vol. 74, No. 9: 4236-4243.
33. Yannoutsos, N., J. N. Ijzermans, C. Harkes, F. Bonthuis, C. Y. Zhou, D. White, R. L. Marquet, and F. Grosveld. 1996. A membrane cofactor protein transgenic mouse model for the study of discordant xenograft rejection [published erratum appears in Genes Cells 1996 August; 1(8): 785]. Genes Cells. 1: 409-419.
34. Naniche, D., G. Varior-Krishnan, F. Cervoni, T. F. Wild, B. Rossi, C. Rabourdin-Combe, and D. Gerlier. 1993. Human membrane cofactor protein (CD46) acts as a cellular receptor for measles virus. J. Virol. 67: 6025-6032.
35. Buynak, E., R. Weibel, W. J. J E, J. Stokes Jr, and M. Hilleman. 1969. Combined live measles, mumps, and rubella virus vaccines. J. Am. Med. Assoc. 207: 2259-2262.
36. Naniche, D., A. Yeh, D. Eto, M. Manchester, R. M. Friedman, and M. B. A. Oldstone. 2000. Evasion of host defenses by measles virus: wild-type measles virus infection interferes with induction of alpha/beta interferon.
37. Garcin, D., P. Latorre, and D. Kolakofsky. 1999. Sendai virus C proteins counteract the interferon-mediated induction of an antiviral state. J. Virol. 73: 6559-6565.

The invention claimed is:

1. An expression vector for producing an infectious recombinant live-attenuated measles virus comprising:
   A) a nucleotide sequence encoding a full length antigenomic (+)RNA strand of the live-attenuated measles virus;

B) a T7 promoter sequence comprising a GGG motif at its 3' end, operably linked to the nucleotide sequence of A);

C) a hammerhead ribozyme sequence located adjacent to the GGG motif at one end and adjacent to the first nucleotide of the nucleotide sequence encoding the full length anti-genomic (+)RNA strand of the measles virus at the other end;

D) a T7 terminator sequence operably linked to the nucleotide sequence of A);

E) a sequence of a hepatitis delta virus ribozyme located adjacent to the last nucleotide of the nucleotide sequence encoding the full length anti-genomic (+)RNA strand of the measles virus; and F) a heterologous coding sequence encoding a heterologous amino acid sequence.

2. The expression vector of claim 1, wherein the infectious recombinant measles virus is a recombinant Schwarz strain.

3. The expression vector of claim 1, wherein the infectious recombinant measles virus is a recombinant Moraten strain.

4. The expression vector of claim 2, wherein the full length antigenomic (+)RNA strand has the sequence extending from position 83 to position 15976 of SEQ ID NO: 82.

5. The expression vector of claim 2, wherein the hammerhead ribozyme sequence has the sequence extending from position 29 to position 82 of SEQ ID NO: 82.

6. The expression vector of claim 2, comprising the nucleotide sequence extending from nucleotide 83 to nucleotide 15976 of the sequence of SEQ ID NO: 82.

7. The expression vector of claim 2, comprising the nucleotide sequence of SEQ ID NO: 82.

8. The expression vector of claim 2, comprising the nucleotide sequence extending from nucleotide 29 to nucleotide 16202 of the sequence of SEQ ID NO: 82.

9. The expression vector of claim 2, comprising the nucleotide sequence extending from nucleotide 26 to nucleotide 16202 of the sequence of SEQ ID NO: 82.

10. The expression vector of claim 2, comprising the nucleotide sequence extending from nucleotide 9 to nucleotide 16202 of the sequence of SEQ ID NO: 82.

11. The expression vector of claim 1, wherein the heterologous coding sequence is cloned within the nucleotide sequence encoding the full length antigenomic (+)RNA strand of the measles virus at a position upstream of the N gene of the measles virus.

12. The expression vector of claim 1, wherein the heterologous coding sequence is cloned between the P and M gene of the measles virus.

13. The expression vector of claim 1, wherein the heterologous coding sequence is cloned between the H and L genes of the measles virus.

14. The expression vector of claim 1, wherein the heterologous coding sequence codes for an immunogenic sequence of a pathogen.

* * * * *